(12) United States Patent
Brugger et al.

(10) Patent No.: US 10,895,339 B2
(45) Date of Patent: Jan. 19, 2021

(54) METHODS, DEVICES, AND SYSTEMS FOR COUPLING FLUID LINES

(71) Applicant: Nxstage Medical, Inc., Lawrence, MA (US)

(72) Inventors: James M. Brugger, Newburyport, MA (US); Dennis M. Treu, Castle Rock, CO (US); David S. Utterberg, Seattle, WA (US)

(73) Assignee: NxStage Medical, Inc., Lawrence, MA (US)

( * ) Notice: Subject to any disclaimer, the term of this patent is extended or adjusted under 35 U.S.C. 154(b) by 40 days.

(21) Appl. No.: 16/185,658

(22) Filed: Nov. 9, 2018

(65) Prior Publication Data

US 2019/0078714 A1   Mar. 14, 2019

Related U.S. Application Data

(62) Division of application No. 15/852,321, filed on Dec. 22, 2017, now Pat. No. 10,221,975, which is a
(Continued)

(51) Int. Cl.
*F16L 35/00* (2006.01)
*F16L 39/02* (2006.01)
(Continued)

(52) U.S. Cl.
CPC .......... *F16L 35/00* (2013.01); *A61M 39/1011* (2013.01); *F16L 39/02* (2013.01);
(Continued)

(58) Field of Classification Search
CPC ......... F16L 35/00; F16L 39/02; F16L 41/023; F16L 25/14; F16L 13/141; F16L 2201/10;
(Continued)

(56) References Cited

U.S. PATENT DOCUMENTS 470,237 A   3/1892   Freeman
3,429,343 A   2/1969   Harry
(Continued)

FOREIGN PATENT DOCUMENTS

DE   20318583 U1   1/2005
DE   102010018954 A1   10/2011
(Continued)

OTHER PUBLICATIONS

Office Action (Communication Pursuant to Article 94(3) EPC) dated Nov. 21, 2019 for European Patent Application No. 18181925.1.
(Continued)

*Primary Examiner* — Jessie T Fonseca
(74) *Attorney, Agent, or Firm* — Potomac Law Group, PLLC; George Dolina

(57) ABSTRACT

The disclosed subject matter includes embodiments of fluid couplings that prevent or discourage misconnection of fluid lines. In embodiments, a coupling device may be configured according to lookup table that defines compatible configurations of connectors. The configurations may be based on the presence and absence of interference members at standardized locations on the respective connectors. The interference members may include posts that mechanically interfere with other posts, but can be inserted into holes when two connectors have a compatible configuration.

9 Claims, 14 Drawing Sheets

Related U.S. Application Data division of application No. 14/123,008, filed as application No. PCT/US2012/041765 on Jun. 8, 2012, now Pat. No. 9,879,807.

(60) Provisional application No. 61/494,504, filed on Jun. 8, 2011.

(51) Int. Cl.
   *F16L 41/02* (2006.01)
   *A61M 39/10* (2006.01)
(52) U.S. Cl.
   CPC .......... *F16L 41/023* (2013.01); *A61M 39/105* (2013.01); *A61M 2039/1027* (2013.01); *A61M 2039/1094* (2013.01); *F16L 2201/10* (2013.01)
(58) Field of Classification Search
   CPC ...... A61M 39/1011; A61M 2039/1027; A61M 39/105; A61M 2039/1094; B61G 5/08
   USPC ............ 285/12, 131.1, 132.1, 330, 913, 914
   See application file for complete search history.

(56) References Cited

U.S. PATENT DOCUMENTS

| | | | |
|---|---|---|---|
| 3,523,700 | A | 8/1970 | Palmer |
| 4,150,673 | A | 4/1979 | Watt |
| 4,211,439 | A | 7/1980 | Moldestad |
| 4,619,640 | A | 10/1986 | Potolsky et al. |
| 4,676,563 | A | 6/1987 | Curlett et al. |
| 4,699,298 | A | 10/1987 | Grant et al. |
| 4,769,615 | A | 9/1988 | Liberman |
| 4,790,567 | A | 12/1988 | Kawano et al. |
| 4,900,065 | A | 2/1990 | Houck |
| 5,725,511 | A | 3/1998 | Urrutia |
| 5,921,965 | A | 7/1999 | Blei |
| 6,007,107 | A | 12/1999 | Kazarian |
| 6,168,209 | B1 | 1/2001 | Cope et al. |
| 6,402,207 | B1 | 6/2002 | Segal et al. |
| 6,481,756 | B1 | 11/2002 | Field et al. |
| 6,499,719 | B1 | 12/2002 | Clancy et al. |
| 6,523,861 | B1 | 2/2003 | Clancy et al. |
| RE38,204 | E | 7/2003 | Kazarian |
| 8,092,409 | B2 | 1/2012 | Mros et al. |
| 2002/0183763 | A1 | 12/2002 | Callol et al. |
| 2004/0217586 | A1 | 11/2004 | Mastropaolo |
| 2005/0082828 | A1 | 4/2005 | Wicks et al. |
| 2005/0184264 | A1 | 8/2005 | Tesluk et al. |
| 2006/0047251 | A1 | 3/2006 | Smith et al. |
| 2008/0048436 | A1 | 2/2008 | Matkovich et al. |
| 2008/0077063 | A1 | 3/2008 | Meyer et al. |
| 2008/0077176 | A1 | 3/2008 | Hanlon et al. |
| 2008/0318477 | A1 | 12/2008 | Standke |
| 2009/0149077 | A1 | 6/2009 | Trimbom et al. |
| 2010/0057015 | A1 | 3/2010 | Lee |
| 2010/0283238 | A1 | 11/2010 | Deighan et al. |
| 2011/0144626 | A1 | 6/2011 | Hall |
| 2011/0203582 | A1 | 8/2011 | Hacke et al. |
| 2013/0147185 | A1 | 6/2013 | Tsao |
| 2014/0001748 | A1 | 1/2014 | Ignaczak et al. |
| 2014/0171855 | A1 | 6/2014 | Mastri et al. |
| 2014/0299221 | A1 | 10/2014 | Lopez et al. |

FOREIGN PATENT DOCUMENTS

| | | |
|---|---|---|
| EP | 0405907 A1 | 1/1991 |
| EP | 0821444 A2 | 1/1998 |
| EP | 0821444 B1 | 2/2003 |
| EP | 2130485 A1 | 12/2009 |
| JP | H10165943 | 6/1998 |

OTHER PUBLICATIONS

Examination Report for European Patent Application No. 12796383.3 dated Jun. 1, 2016.
Extended European Search Report for European Application No. 12796383.3 dated Feb. 24, 2015.
International Search Report and Written Opinion for International Application No. PCT/US12/41765, dated Aug. 28, 2012.
Office Action for Japanese Application No. 2014-514912 dated May 10, 2016 including English language translation.
Office Action dated Aug. 26, 2014, in UK Patent Application No. GB1321373.1.
Office Action dated Nov. 17, 2014, in UK Patent Application No. GB1321373.1.
Summons to Attend Oral Proceedings Pursuant to Rule 115(1) EPC for European Patent No. 12796383.3 dated Oct. 2, 2017.
Colder Products Company, "CPC Product Catalog," Jun. 1, 2007, retrieved Jun. 3, 2020 from https://content.cpcworldwide.com/Portals/0/Library/Resources/literature/Catalogs/Documents/Catalogs/Colder Products_Company_Catalog_ 11x17.pdf>.
International Search Report and Written Opinion dated Aug. 11, 2020 for International Patent Application No. PCT/US2020/027051.

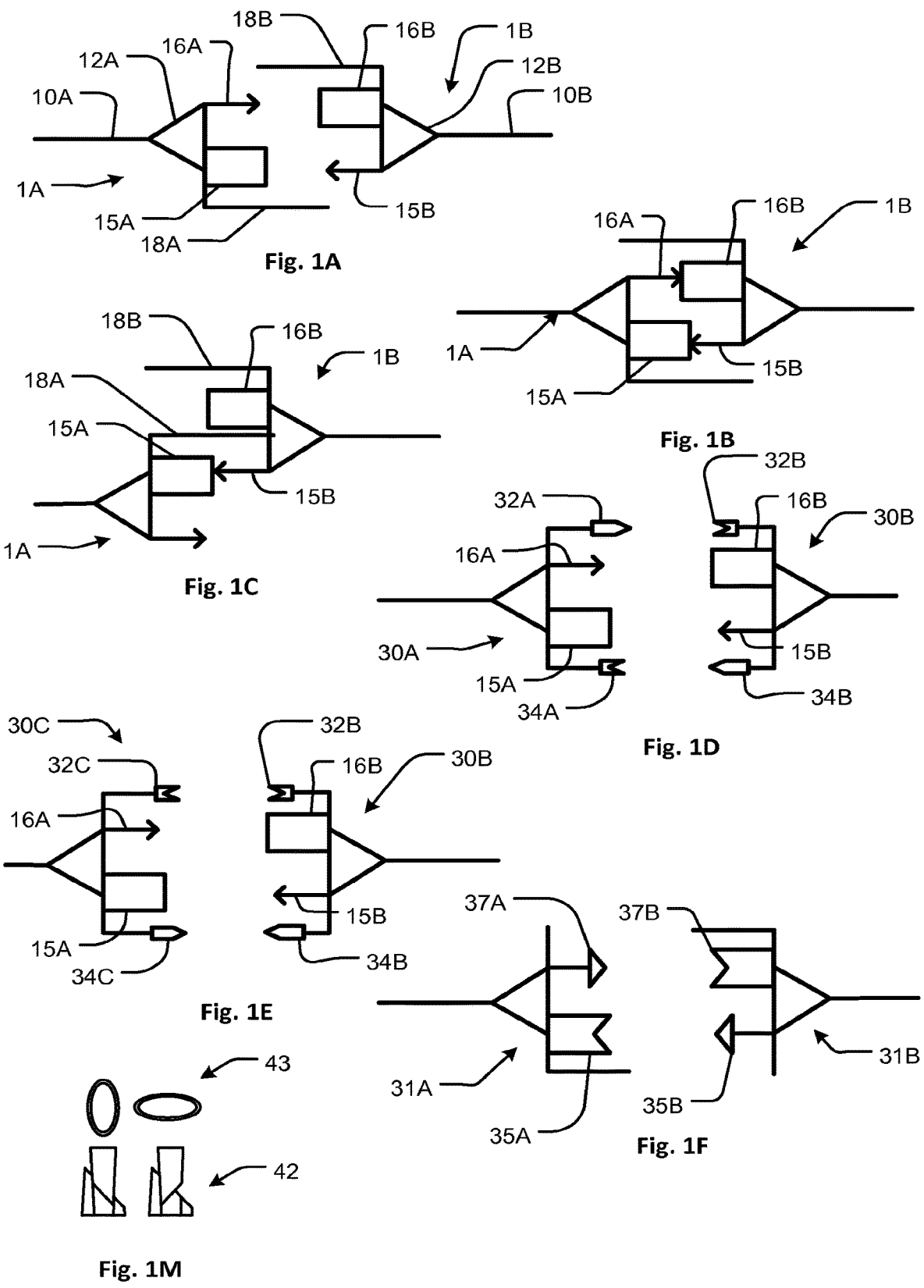

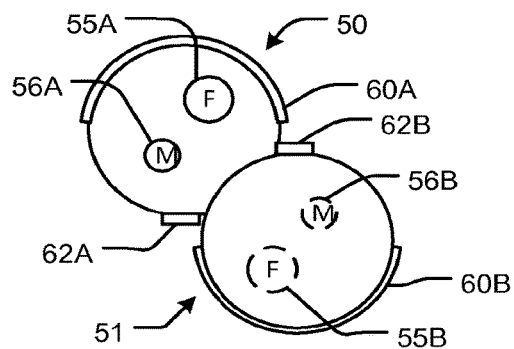
Fig. 1G
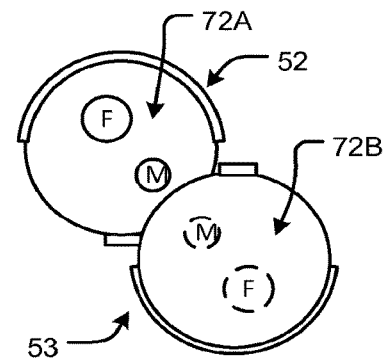
Fig. 1H
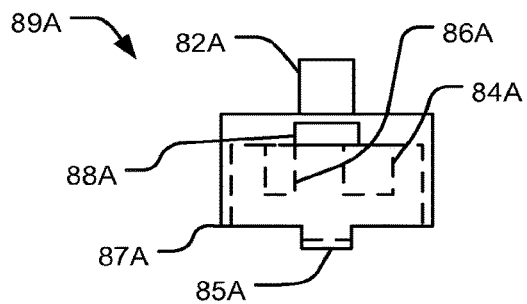
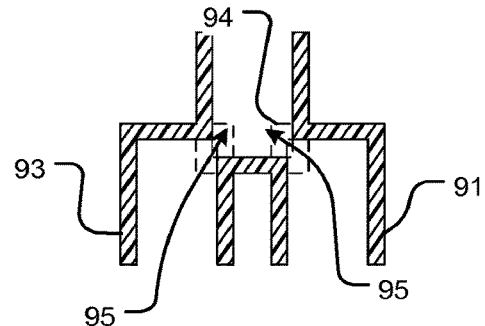
Fig. 1K
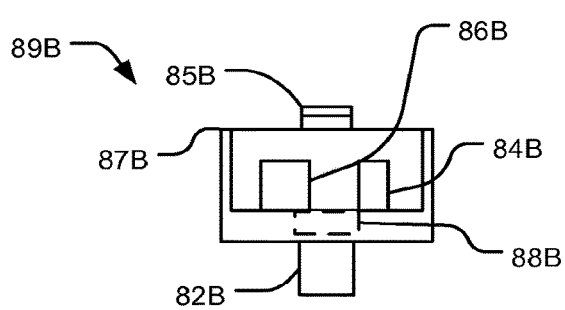
Fig. 1J
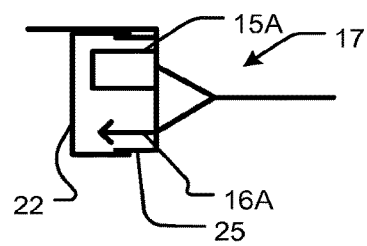
Fig. 1L
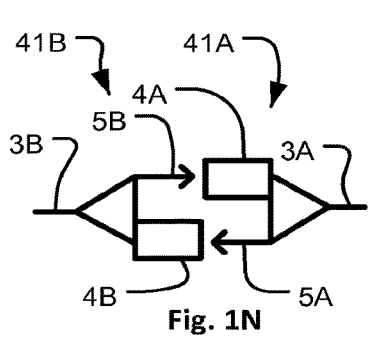
Fig. 1N
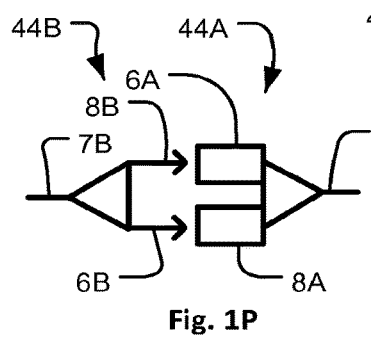
Fig. 1P
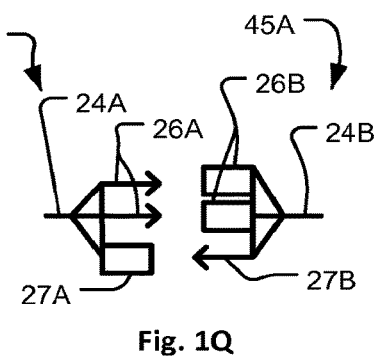
Fig. 1Q

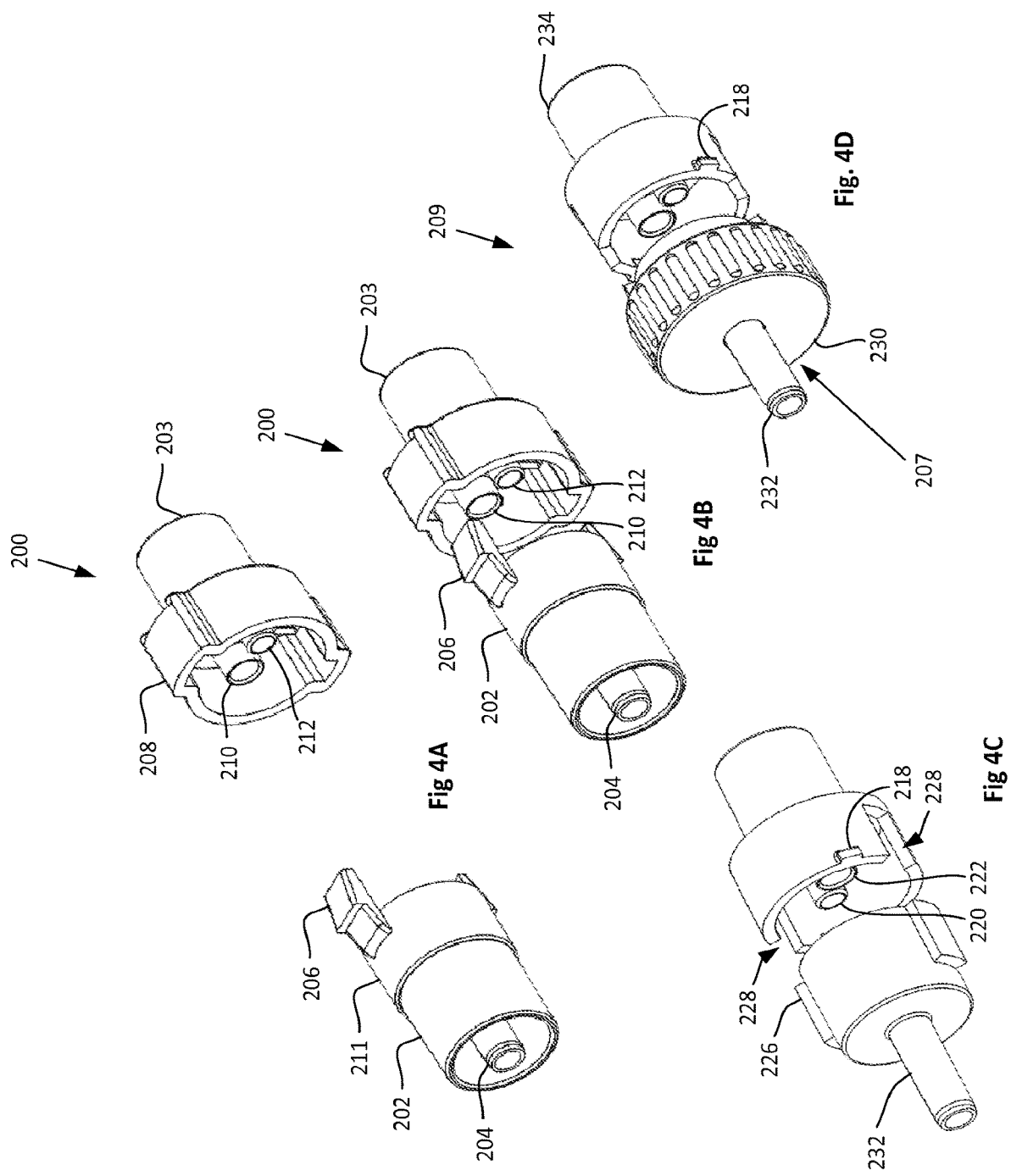

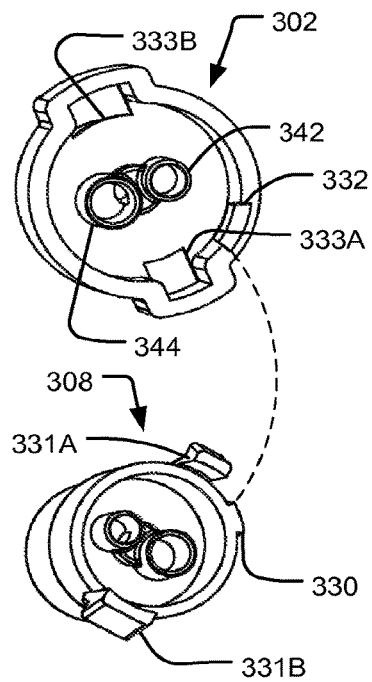
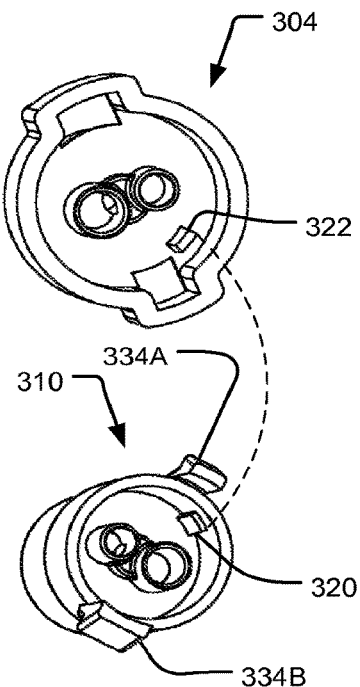
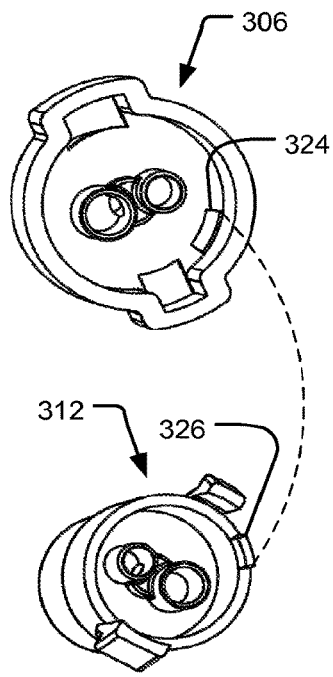
Fig. 5A  Fig. 5B  Fig. 5C
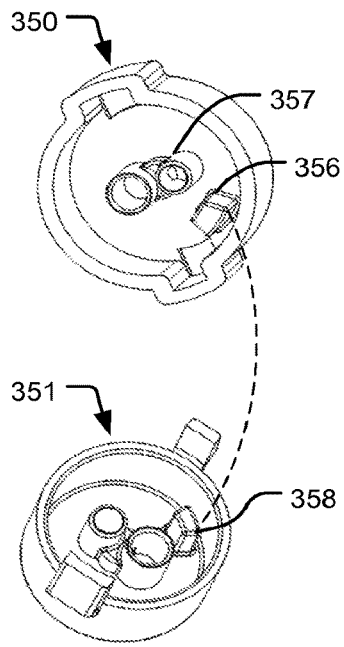
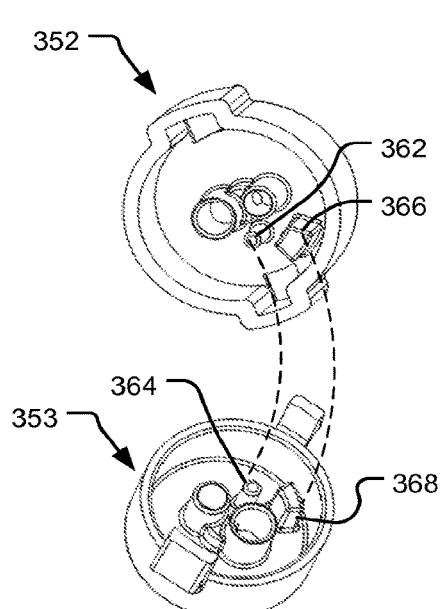
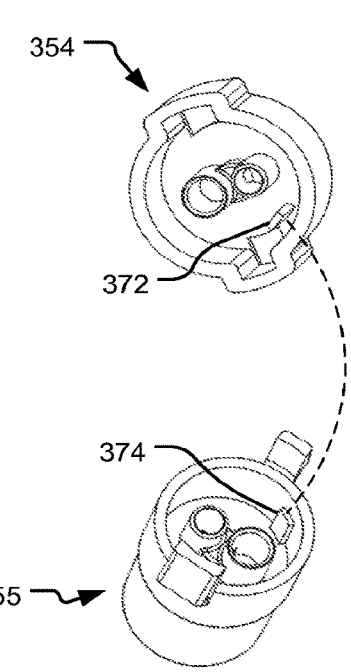
Fig. 5D  Fig. 5E  Fig. 5F

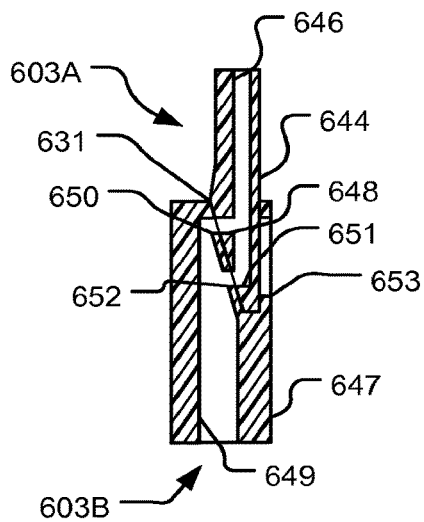
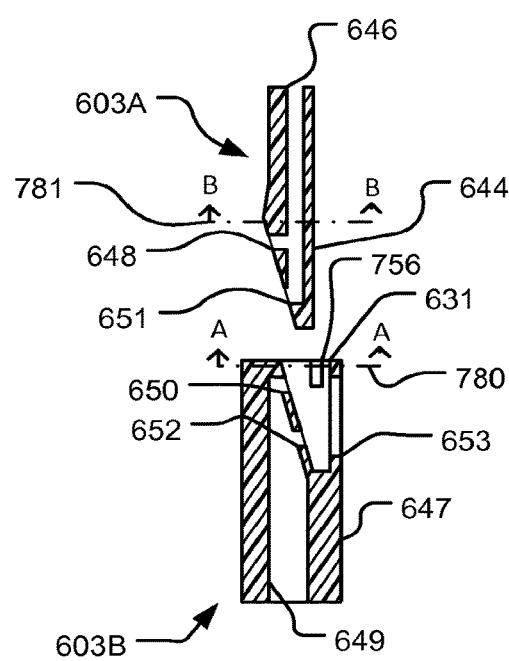
Fig. 12A
Fig 12B
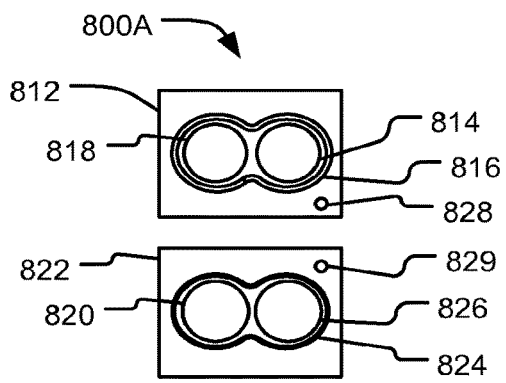
Fig. 13
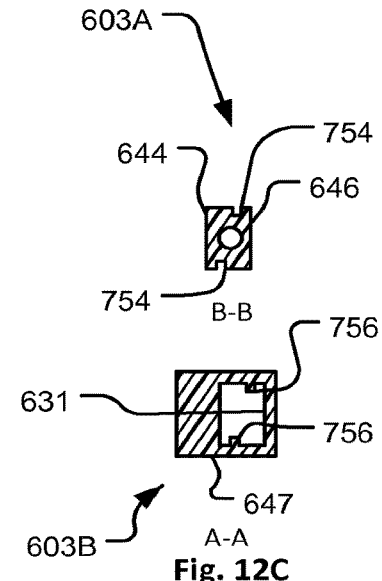
Fig. 12C
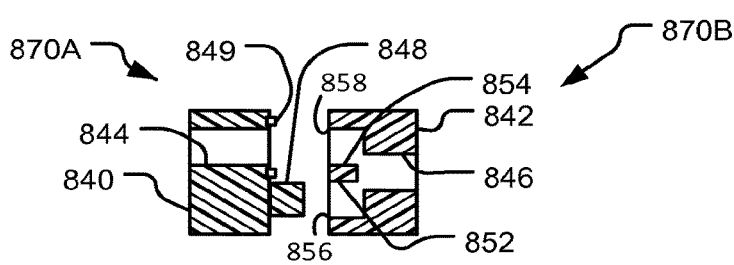
Fig. 14A
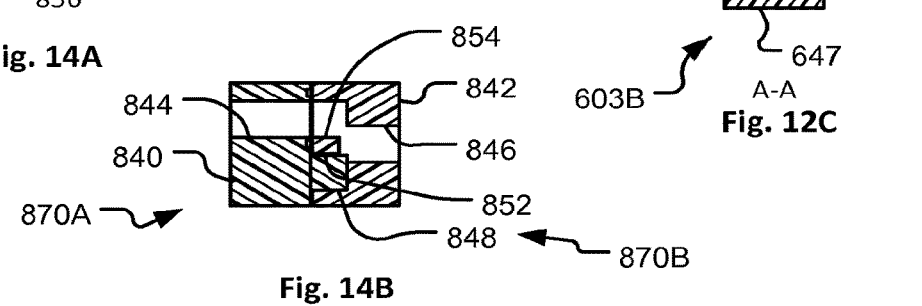
Fig. 14B X=incompatible
Blank=compatible

| A | | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|---|---|---|---|---|---|---|---|---|---|---|---|---|---|---|---|---|
| B | binary | 100000 | 100001 | 100010 | 100011 | 100100 | 100101 | 100110 | 100111 | 101000 | 101001 | 101010 | 101011 | 101100 | 101101 | 101110 | 101111 | 110000 | 110001 | 110010 | 110011 | 110100 | 110101 | 110110 | 110111 | 111000 | 111001 | 111010 | 111011 | 111100 | 111101 | 111110 | 111111 |
| 0 | 000000 | | | | | | | | | | | | | | | | | | | | | | | | | | | | | | | | |
| 1 | 000001 | x | | x | | x | | x | | x | | x | | x | | x | | x | | x | | x | | x | | x | | x | | x | | x | |
| 2 | 000010 | | x | x | | | x | x | | | x | x | | | x | x | | | x | x | | | x | x | | | x | x | | | x | x | |
| 3 | 000011 | x | x | x | | x | x | x | | x | x | x | | x | x | x | | x | x | x | | x | x | x | | x | x | x | | x | x | x | |
| 4 | 000100 | | | | x | x | x | x | | | | | x | x | x | x | | | | | x | x | x | x | | | | | x | x | x | x | |
| 5 | 000101 | x | | x | x | x | x | x | | x | | x | x | x | x | x | | x | | x | x | x | x | x | | x | | x | x | x | x | x | |
| 6 | 000110 | | x | x | x | x | x | x | | | x | x | x | x | x | x | | | x | x | x | x | x | x | | | x | x | x | x | x | x | |
| 7 | 000111 | x | x | x | x | x | x | x | | x | x | x | x | x | x | x | | x | x | x | x | x | x | x | | x | x | x | x | x | x | x | |
| 8 | 001000 | | | | | | | | x | x | x | x | x | x | x | x | | | | | | | | | x | x | x | x | x | x | x | x | |
| 9 | 001001 | x | | x | | x | | x | x | x | x | x | x | x | x | x | | x | | x | | x | | x | x | x | x | x | x | x | x | x | |
| 10 | 001010 | | x | x | | | x | x | x | x | x | x | x | x | x | x | | | x | x | | | x | x | x | x | x | x | x | x | x | x | |
| 11 | 001011 | x | x | x | | x | x | x | x | x | x | x | x | x | x | x | | x | x | x | | x | x | x | x | x | x | x | x | x | x | x | |
| 12 | 001100 | | | | x | x | x | x | x | x | x | x | x | x | x | x | | | | | x | x | x | x | x | x | x | x | x | x | x | x | |
| 13 | 001101 | x | | x | x | x | x | x | x | x | x | x | x | x | x | x | | x | | x | x | x | x | x | x | x | x | x | x | x | x | x | |
| 14 | 001110 | | x | x | x | x | x | x | x | x | x | x | x | x | x | x | | | x | x | x | x | x | x | x | x | x | x | x | x | x | x | |
| 15 | 001111 | x | x | x | x | x | x | x | x | x | x | x | x | x | x | x | | x | x | x | x | x | x | x | x | x | x | x | x | x | x | x | |
| 16 | 010000 | | | | | | | | | | | | | | | | x | x | x | x | x | x | x | x | x | x | x | x | x | x | x | x | |
| 17 | 010001 | x | | x | | x | | x | | x | | x | | x | | x | x | x | x | x | x | x | x | x | x | x | x | x | x | x | x | x | |
| 18 | 010010 | | x | x | | | x | x | | | x | x | | | x | x | x | x | x | x | x | x | x | x | x | x | x | x | x | x | x | x | |
| 19 | 010011 | x | x | x | | x | x | x | | x | x | x | | x | x | x | x | x | x | x | x | x | x | x | x | x | x | x | x | x | x | x | |
| 20 | 010100 | | | | x | x | x | x | | | | | x | x | x | x | x | x | x | x | x | x | x | x | x | x | x | x | x | x | x | x | |
| 21 | 010101 | x | | x | x | x | x | x | | x | | x | x | x | x | x | x | x | x | x | x | x | x | x | x | x | x | x | x | x | x | x | |
| 22 | 010110 | | x | x | x | x | x | x | | | x | x | x | x | x | x | x | x | x | x | x | x | x | x | x | x | x | x | x | x | x | x | |
| 23 | 010111 | x | x | x | x | x | x | x | | x | x | x | x | x | x | x | x | x | x | x | x | x | x | x | x | x | x | x | x | x | x | x | |
| 24 | 011000 | | | | | | | | x | x | x | x | x | x | x | x | x | x | x | x | x | x | x | x | x | x | x | x | x | x | x | x | |
| 25 | 011001 | x | | x | | x | | x | x | x | x | x | x | x | x | x | x | x | x | x | x | x | x | x | x | x | x | x | x | x | x | x | |
| 26 | 011010 | | x | x | | | x | x | x | x | x | x | x | x | x | x | x | x | x | x | x | x | x | x | x | x | x | x | x | x | x | x | |
| 27 | 011011 | x | x | x | | x | x | x | x | x | x | x | x | x | x | x | x | x | x | x | x | x | x | x | x | x | x | x | x | x | x | x | |
| 28 | 011100 | | | | x | x | x | x | x | x | x | x | x | x | x | x | x | x | x | x | x | x | x | x | x | x | x | x | x | x | x | x | |
| 29 | 011101 | x | | x | x | x | x | x | x | x | x | x | x | x | x | x | x | x | x | x | x | x | x | x | x | x | x | x | x | x | x | x | |
| 30 | 011110 | | x | x | x | x | x | x | x | x | x | x | x | x | x | x | x | x | x | x | x | x | x | x | x | x | x | x | x | x | x | x | |
| 31 | 011111 | x | x | x | x | x | x | x | x | x | x | x | x | x | x | x | x | x | x | x | x | x | x | x | x | x | x | x | x | x | x | x | |

X=incompatible
Blank=compatible

Fig. 15C

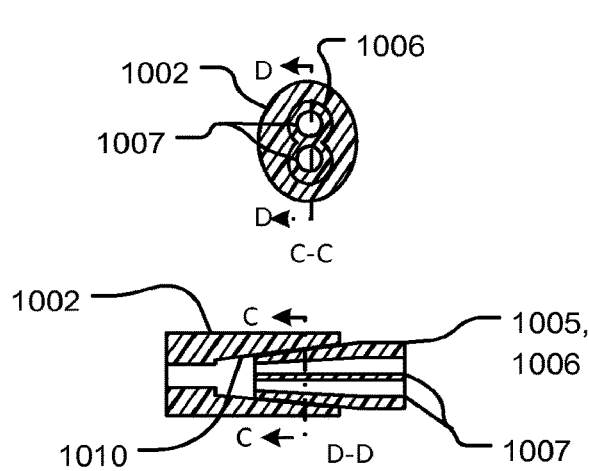

Fig. 14C

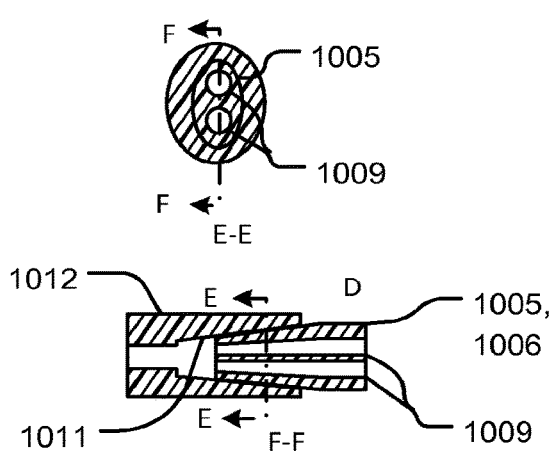

Fig. 14D

| A | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---|---|
| B binary | 000000 | 000001 | 000010 | 000011 | 000100 | 000101 | 000110 | 000111 | 001000 | 001001 | 001010 | 001011 | 001100 | 001101 | 001110 | 001111 | 010000 | 010001 | 010010 | 010011 | 010100 | 010101 | 010110 | 010111 | 011000 | 011001 | 011010 | 011011 | 011100 | 011101 | 011110 | 011111 |
| 32 100000 |  |  |  |  |  |  |  |  |  |  |  |  |  |  |  |  |  |  |  |  |  |  |  |  |  |  |  |  |  |  |  |  |
| 33 100001 |  | X |  | X |  | X |  | X |  | X |  | X |  | X |  | X |  | X |  | X |  | X |  | X |  | X |  | X |  | X |  | X |
| 34 100010 |  |  | X | X |  |  | X | X |  |  | X | X |  |  | X | X |  |  | X | X |  |  | X | X |  |  | X | X |  |  | X | X |
| 35 100011 |  | X | X | X |  | X | X | X |  | X | X | X |  | X | X | X |  | X | X | X |  | X | X | X |  | X | X | X |  | X | X | X |
| 36 100100 |  |  |  |  | X | X | X | X |  |  |  |  | X | X | X | X |  |  |  |  | X | X | X | X |  |  |  |  | X | X | X | X |
| 37 100101 |  | X |  | X | X | X | X | X |  | X |  | X | X | X | X | X |  | X |  | X | X | X | X | X |  | X |  | X | X | X | X | X |
| 38 100110 |  |  | X | X | X | X | X | X |  |  | X | X | X | X | X | X |  |  | X | X | X | X | X | X |  |  | X | X | X | X | X | X |
| 39 100111 |  | X | X | X | X | X | X | X |  | X | X | X | X | X | X | X |  | X | X | X | X | X | X | X |  | X | X | X | X | X | X | X |
| 40 101000 |  |  |  |  |  |  |  |  | X | X | X | X | X | X | X | X |  |  |  |  |  |  |  |  | X | X | X | X | X | X | X | X |
| 41 101001 |  | X |  | X |  | X |  | X | X | X | X | X | X | X | X | X |  | X |  | X |  | X |  | X | X | X | X | X | X | X | X | X |
| 42 101010 |  |  | X | X |  |  | X | X | X | X | X | X | X | X | X | X |  |  | X | X |  |  | X | X | X | X | X | X | X | X | X | X |
| 43 101011 |  | X | X | X |  | X | X | X | X | X | X | X | X | X | X | X |  | X | X | X |  | X | X | X | X | X | X | X | X | X | X | X |
| 44 101100 |  |  |  | X | X | X | X | X | X | X | X | X | X | X | X | X |  |  |  | X | X | X | X | X | X | X | X | X | X | X | X | X |
| 45 101101 |  | X |  | X | X | X | X | X | X | X | X | X | X | X | X | X |  | X |  | X | X | X | X | X | X | X | X | X | X | X | X | X |
| 46 101110 |  |  | X | X | X | X | X | X | X | X | X | X | X | X | X | X |  |  | X | X | X | X | X | X | X | X | X | X | X | X | X | X |
| 47 101111 |  | X | X | X | X | X | X | X | X | X | X | X | X | X | X | X |  | X | X | X | X | X | X | X | X | X | X | X | X | X | X | X |
| 48 110000 |  |  |  |  |  |  |  |  |  |  |  |  |  |  |  | O | X | X | X | X | X | X | X | X | X | X | X | X | X | X | X | X |
| 49 110001 |  | X |  | X |  | X |  | X |  | X |  | X |  | X |  | X | X | X | X | X | X | X | X | X | X | X | X | X | X | X | X | X |
| 50 110010 |  |  | X | X |  |  | X | X |  |  | X | X |  |  | X | X | X | X | X | X | X | X | X | X | X | X | X | X | X | X | X | X |
| 51 110011 |  | X | X | X |  | X | X | X |  | X | X | X |  | X | X | X | X | X | X | X | X | X | X | X | X | X | X | X | X | X | X | X |
| 52 110100 |  |  |  |  | X | X | X | X |  |  |  |  | X | X | X | X | X | X | X | X | X | X | X | X | X | X | X | X | X | X | X | X |
| 53 110101 |  | X |  | X | X | X | X | X |  | X |  | X | X | X | X | X | X | X | X | X | X | X | X | X | X | X | X | X | X | X | X | X |
| 54 110110 |  |  | X | X | X | X | X | X |  |  | X | X | X | X | X | X | X | X | X | X | X | X | X | X | X | X | X | X | X | X | X | X |
| 55 110111 |  | X | X | X | X | X | X | X |  | X | X | X | X | X | X | X | X | X | X | X | X | X | X | X | X | X | X | X | X | X | X | X |
| 56 111000 |  |  |  |  |  |  |  |  | X | X | X | X | X | X | X | X | X | X | X | X | X | X | X | X | X | X | X | X | X | X | X | X |
| 57 111001 |  | X |  | X |  | X |  | X | X | X | X | X | X | X | X | X | X | X | X | X | X | X | X | X | X | X | X | X | X | X | X | X |
| 58 111010 |  |  | X | X |  |  | X | X | X | X | X | X | X | X | X | X | X | X | X | X | X | X | X | X | X | X | X | X | X | X | X | X |
| 59 111011 |  | X | X | X |  | X | X | X | X | X | X | X | X | X | X | X | X | X | X | X | X | X | X | X | X | X | X | X | X | X | X | X |
| 60 111100 |  |  |  | X | X | X | X | X | X | X | X | X | X | X | X | X | X | X | X | X | X | X | X | X | X | X | X | X | X | X | X | X |
| 61 111101 |  | X |  | X | X | X | X | X | X | X | X | X | X | X | X | X | X | X | X | X | X | X | X | X | X | X | X | X | X | X | X | X |
| 62 111110 |  |  | X | X | X | X | X | X | X | X | X | X | X | X | X | X | X | X | X | X | X | X | X | X | X | X | X | X | X | X | X | X |
| 63 111111 |  | X | X | X | X | X | X | X | X | X | X | X | X | X | X | X | X | X | X | X | X | X | X | X | X | X | X | X | X | X | X | X |

Fig. 15D

X=incompatible
Blank=compatible

| A | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|---|---|---|---|---|---|---|---|---|---|---|---|---|---|---|---|
| B binary | 100000 | 100001 | 100010 | 100011 | 100100 | 100101 | 100110 | 100111 | 101000 | 101001 | 101010 | 101011 | 101100 | 101101 | 101110 | 101111 | 110000 | 110001 | 110010 | 110011 | 110100 | 110101 | 110110 | 110111 | 111000 | 111001 | 111010 | 111011 | 111100 | 111101 | 111110 | 111111 |
| 32 100000 | X | X | X | X | X | X | X | X | X | X | X | X | X | X | X | X | X | X | X | X | X | X | X | X | X | X | X | X | X | X | X | X |
| 33 100001 | X | X | X | X | X | X | X | X | X | X | X | X | X | X | X | X | X | X | X | X | X | X | X | X | X | X | X | X | X | X | X | X |
| 34 100010 | X | X | X | X | X | X | X | X | X | X | X | X | X | X | X | X | X | X | X | X | X | X | X | X | X | X | X | X | X | X | X | X |
| 35 100011 | X | X | X | X | X | X | X | X | X | X | X | X | X | X | X | X | X | X | X | X | X | X | X | X | X | X | X | X | X | X | X | X |
| 36 100100 | X | X | X | X | X | X | X | X | X | X | X | X | X | X | X | X | X | X | X | X | X | X | X | X | X | X | X | X | X | X | X | X |
| 37 100101 | X | X | X | X | X | X | X | X | X | X | X | X | X | X | X | X | X | X | X | X | X | X | X | X | X | X | X | X | X | X | X | X |
| 38 100110 | X | X | X | X | X | X | X | X | X | X | X | X | X | X | X | X | X | X | X | X | X | X | X | X | X | X | X | X | X | X | X | X |
| 39 100111 | X | X | X | X | X | X | X | X | X | X | X | X | X | X | X | X | X | X | X | X | X | X | X | X | X | X | X | X | X | X | X | X |
| 40 101000 | X | X | X | X | X | X | X | X | X | X | X | X | X | X | X | X | X | X | X | X | X | X | X | X | X | X | X | X | X | X | X | X |
| 41 101001 | X | X | X | X | X | X | X | X | X | X | X | X | X | X | X | X | X | X | X | X | X | X | X | X | X | X | X | X | X | X | X | X |
| 42 101010 | X | X | X | X | X | X | X | X | X | X | X | X | X | X | X | X | X | X | X | X | X | X | X | X | X | X | X | X | X | X | X | X |
| 43 101011 | X | X | X | X | X | X | X | X | X | X | X | X | X | X | X | X | X | X | X | X | X | X | X | X | X | X | X | X | X | X | X | X |
| 44 101100 | X | X | X | X | X | X | X | X | X | X | X | X | X | X | X | X | X | X | X | X | X | X | X | X | X | X | X | X | X | X | X | X |
| 45 101101 | X | X | X | X | X | X | X | X | X | X | X | X | X | X | X | X | X | X | X | X | X | X | X | X | X | X | X | X | X | X | X | X |
| 46 101110 | X | X | X | X | X | X | X | X | X | X | X | X | X | X | X | X | X | X | X | X | X | X | X | X | X | X | X | X | X | X | X | X |
| 47 101111 | X | X | X | X | X | X | X | X | X | X | X | X | X | X | X | X | X | X | X | X | X | X | X | X | X | X | X | X | X | X | X | X |
| 48 110000 | X | X | X | X | X | X | X | X | X | X | X | X | X | X | X | X | (X) | X | X | X | X | X | X | X | X | X | X | X | X | X | X | X |
| 49 110001 | X | X | X | X | X | X | X | X | X | X | X | X | X | X | X | X | X | X | X | X | X | X | X | X | X | X | X | X | X | X | X | X |
| 50 110010 | X | X | X | X | X | X | X | X | X | X | X | X | X | X | X | X | X | X | X | X | X | X | X | X | X | X | X | X | X | X | X | X |
| 51 110011 | X | X | X | X | X | X | X | X | X | X | X | X | X | X | X | X | X | X | X | X | X | X | X | X | X | X | X | X | X | X | X | X |
| 52 110100 | X | X | X | X | X | X | X | X | X | X | X | X | X | X | X | X | X | X | X | X | X | X | X | X | X | X | X | X | X | X | X | X |
| 53 110101 | X | X | X | X | X | X | X | X | X | X | X | X | X | X | X | X | X | X | X | X | X | X | X | X | X | X | X | X | X | X | X | X |
| 54 110110 | X | X | X | X | X | X | X | X | X | X | X | X | X | X | X | X | X | X | X | X | X | X | X | X | X | X | X | X | X | X | X | X |
| 55 110111 | X | X | X | X | X | X | X | X | X | X | X | X | X | X | X | X | X | X | X | X | X | X | X | X | X | X | X | X | X | X | X | X |
| 56 111000 | X | X | X | X | X | X | X | X | X | X | X | X | X | X | X | X | X | X | X | X | X | X | X | X | X | X | X | X | X | X | X | X |
| 57 111001 | X | X | X | X | X | X | X | X | X | X | X | X | X | X | X | X | X | X | X | X | X | X | X | X | X | X | X | X | X | X | X | X |
| 58 111010 | X | X | X | X | X | X | X | X | X | X | X | X | X | X | X | X | X | X | X | X | X | X | X | X | X | X | X | X | X | X | X | X |
| 59 111011 | X | X | X | X | X | X | X | X | X | X | X | X | X | X | X | X | X | X | X | X | X | X | X | X | X | X | X | X | X | X | X | X |
| 60 111100 | X | X | X | X | X | X | X | X | X | X | X | X | X | X | X | X | X | X | X | X | X | X | X | X | X | X | X | X | X | X | X | X |
| 61 111101 | X | X | X | X | X | X | X | X | X | X | X | X | X | X | X | X | X | X | X | X | X | X | X | X | X | X | X | X | X | X | X | X |
| 62 111110 | X | X | X | X | X | X | X | X | X | X | X | X | X | X | X | X | X | X | X | X | X | X | X | X | X | X | X | X | X | X | X | X |
| 63 111111 | X | X | X | X | X | X | X | X | X | X | X | X | X | X | X | X | X | X | X | X | X | X | X | X | X | X | X | X | X | X | X | X |

Fig. 15E

X=incompatible
Blank=compatible

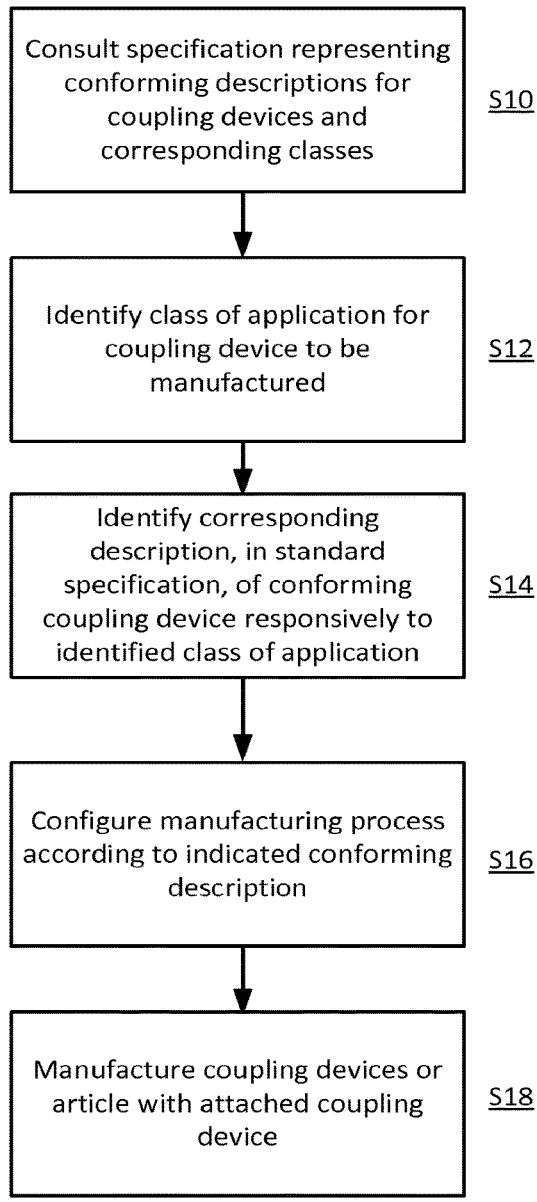
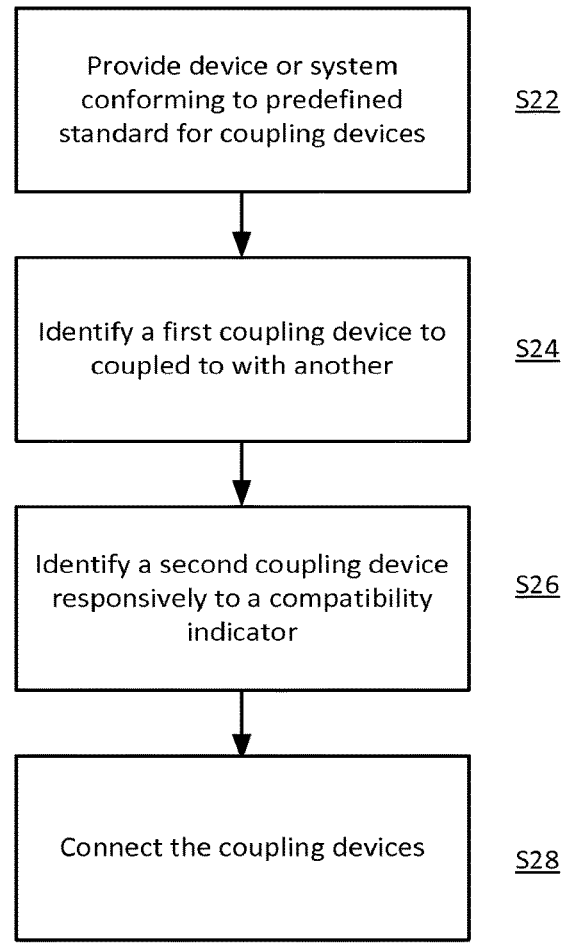
Fig. 16A
Fig. 16B

METHODS, DEVICES, AND SYSTEMS FOR COUPLING FLUID LINES

CROSS-REFERENCE TO RELATED APPLICATIONS

The present application is divisional of U.S. patent application Ser. No. 15/852,321 filed Dec. 22, 2017, which is a divisional of U.S. patent application Ser. No. 14/123,008 filed Feb. 26, 2014, which is a U.S. national stage entry of International Application No. PCT/US2012/041765 filed Jun. 8, 2012, which claims the benefit of U.S. Provisional Application No. 61/494,504 filed on Jun. 8, 2011, all of which are incorporated herein by reference in their entirety.

FIELD

A coupling device, method, and system prevents misconnection of fluid conveyances, for example, gases or liquids.

BACKGROUND

Fluid coupling devices have been made for connecting fluid flow paths, for example, for coupling a source of fluid such as a container to a consuming line or device, such a patient infusion line. Fluid line sources and sinks may include those for gases or liquids or even aerosol solids, multiphase flows, pressurized or unpressurized fluids, fluidized flows of solids such as granular material, etc. Many applications involve hazards that may arise when a misconnection is made between inappropriate or mismatched sources, including devices, manifolds, etc. and the consumers. This may occur in environments where multiple fluid sources and consumers are present, for example in a clinical treatment environment with multiple component medicaments and medications which are all supplied through tubes. Often a single treatment device may involve making multiple connections to various sources and consumer portions of a single system. Many of these couplings are provided with quick disconnect coupling members to enable efficient connection and disconnection from the source.

In hospitals and other medical facilities, supplies may be incorporated in manifolds with multiple outlets for supplying gases and/or liquids. Care is required when connecting a supply line to ensure proper connections are made. Misconnections have been known to cause death, such as connecting a pressure line for a blood pressure cuff to an infusion port enabling air to be infused into the patient's blood creating a fatal air embolism. These connectors were compatible and the connection was easily made. Some instances reported in the U.S. Food and Drug Administration (FDA) Maude database also show forced misconnections resulting in patient harm where dissimilar connectors were forced together through operator misuse. The U.S. FDA along with several regulatory standard organizations; International Standards Organization (ISO), Association for the Advancement of Medical Instrumentation (AAMI), and American National Standards Institute, Inc. (ANSI) have been working for several years on finding a solution to these problems. This a difficult problem that is further complicated by the many existing connector systems employed across the wide array of medical products. Many proposed solutions are complex and difficult to manufacture. For example, some require multiple action injection molding and high tolerances. In some applications, there is a need to keep costs as low as possible, such as for disposable sterile medical tubing sets. Other proposed fluid coupling devices are large and cumbersome or difficult to use. Still others are limited in terms of their potential to reveal an improper connection and are also limited in terms of the variety of inter-connectable and non-inter-connectable populations that are enabled by the basic configuration. There is an on-going need for improvements in the field of fluid coupling devices that prevent or discourage mismatched fluid couplings. Known systems are described in U.S. Pat. Nos. 4,211,439, 4,619,640, 4,790,567, 5,725,511, 6,402,207, 6,168,209, 6,007,107, U.S. RE38204, U.S. Pat. No. 6,499,719, and US Patent publications US20060047251, US20080077176, US20110203582, US20100283238, and US20110144626.

SUMMARY

The disclosed subject matter includes embodiments of fluid (including other media such as multiphase flows, fluidized solids, non-rheological fluids, granular material, etc.) coupling devices, methods, and systems that prevent or discourage, or render impossible, the misconnection of connectors attached to other devices or lines including industry standard connectors. Embodiments are more difficult to circumvent, by attachment of improper connectors, than known systems. In embodiments this is accomplished by creating a leak path to the environment, even in the event of attempts to forcibly connect incompatible connectors such as standard connectors.

In embodiments, a coupling device includes connector arrangements in which flow first port is connected to a first coupling device that communicates with furcated channels extending from a common channel that converges the furcated channels to a common port on a second coupling device. In embodiments, two furcating channels each connect to multiple connectors at the interface between the coupling devices. In a particular example, one coupling device may have male connectors, a combination of male and female connectors, or only female connectors. The other coupling device of a same species (i.e., a coupling device that can mate with the one coupling device) has at least one complementary set of connectors. Each coupling device is mated to a compatible coupling device (by compatible, we mean a coupling device of a configuration that may will a complete fluidic connection with it) only when all the multiple connectors (e.g. male and female in this case) are joined to the compatible coupling device, and any interfering elements provided on the coupling devices allow a seal to be formed by the connectors. Note that the connectors may be of any type, the invaginating types of connectors such as would be characterized as male or female, being described merely as examples. For example, butt-type compression seals or other sealing engagements may be employed for any of the connectors used. Alternative embodiments are also described in which instead of multiple connectors, a single non-round connector is used. The single non-round connector may provide for alignment of the coupling device thereby permitting multiple arrangements of interfering elements to be employed.

If any of the connectors of a coupling device is not properly mated to connectors of another coupling device, the improperly mated coupling devices will leak, since the connectors on each side are joined to respective channels. Flow in one completed fluid connection will leak from the incomplete, or absent, connection. In embodiments, the coupling devices may be configured to form compatible and incompatible sets. Compatible coupling devices would ones that are capable of mating and incompatible would not be capable of mating. The various forms may be made by providing an arrangement of the connectors, number of connectors, shape of connectors, or arrangement, shape, type, size, etc. of interfering elements that ensure that any attempt to improperly couple two coupling devices will result in the incomplete mating of one or more of the connectors and thereby cause leakage of the fluid, failure of the coupling to engage, or otherwise cause the attempt to connect to fail.

It will also be evident, from the foregoing and further disclosure, that the system provides for coupling devices that are compatible (capable of mating) with a family of coupling devices that are incompatible with their respective compatible coupling devices that are meant to be compatible. Thus, a master coupling device A may be compatible with coupling devices B and C where B and C are different species. Thus B may be compatible with D and C may be compatible with E, but B may be incompatible with E and C incompatible with D. Thus, a designer may form various interconnection schemes. For example, a fluid source may be made compatible with a variety of different "client" consuming devices by providing it with a master coupling device that fits the species coupling devices attached to the consuming devices. But other fluid sources may be provided each with a species connector that only allow it to be connected, respectively, to one of the clients and prevents it from connecting with the other.

The coupling device system or scheme may be extended in the form of a further set of embodiments in which instead of having two coupling devices each with a furcating channel, only one coupling device has a furcating channel. The other coupling device has a closure for one of the connectors of the coupling device with the furcating channel. The coupling device with the closure has a connector to connect its flow channel to that of the unclosed connector coupling device with the furcating channel. In embodiments, the coupling device with the closure would only be used on safe lines, such as sources of fluids, to prevent the use of rogue connectors on the coupling devices with closures that could be used to convey dangerous fluids to a destination where harm might result, for example bleach to an infusion line.

In embodiments, the effectiveness of the selectivity enforcement and the prevention of a circumvention of the enforcement mechanism by a user are enhanced by the fact that the multiple connectors require that a certain mutual orientation of the connectors is required in order to create a complete and non-leaking connection. To make a complete connection, for example by making the connection of the male of the first connector to the female of the other while simultaneously making the connection of the female of the first connector to the male of the other requires the coupling devices be mutually oriented with respect to each other. By ensuring this orientation, it is possible to provide an array of interference members that can provide various types of selectivity between connectors of different configuration. This is because the interfering elements can be located at selected points that are sure to come into interfering engagement as a result of the requirement that the coupling devices are properly oriented. Note, as mentioned elsewhere, connectors do not necessarily need to be of the male and/or female type.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 1A through 1C show schematically features of embodiment of the disclosed coupling device embodiments which provide benefits including misconnection prevention, manufacturing economies and small size.

FIGS. 1D and 1E illustrate a variation of the coupling device embodiments of FIGS. 1A and 1B that includes interfering features that prevent misconnection.

FIG. 1F illustrates another variation of the coupling device embodiments of FIGS. 1A and 1B that include connector shape features that prevent misconnection of coupling devices.

FIGS. 1G, 1H, and 1J illustrate arrangements of a coupling device that illustrate how angular and/or position mismatch of coupling device can be used to prevent successful mating of incompatible coupling devices.

FIG. 1K illustrates a feature that may be employed in the disclosed embodiments, the feature including a way to form a Y-junction in a two-part single action molded configuration.

FIG. 1L shows a feature in which an annular rim is provided to form a seal with a cap to allow a multiple connector arrangement to be sealed.

FIG. 1M shows complementary connector features according to further embodiments of the disclosed subject matter.

FIGS. 1N, 1P, and 1Q show general coupling device embodiments to illustrate variations.

FIGS. 4A and 4B show an embodiment of coupling system of asymmetric design, particularly illustrating a locking scheme.

FIGS. 4C and 4D show a coupling system with a further locking scheme.

FIGS. 5A through 5F show various embodiments of coupling system of asymmetric design, particularly illustrating various interference schemes to make all but proper connections difficult or impossible to make.

FIGS. 12A-12C and 13 show alternative mechanisms for mating coupling devices and other alternative features.

FIGS. 14A and 14B show an alternative scheme that may be used to form various species of coupling devices.

FIGS. 14C and 14D show embodiments in which a coupling device has two channels that connect to a single channel forming a double to single connector embodiment.

FIGS. 15A to 15E further describe a simple scheme having six interference elements and how they give rise to many species of compatible and incompatible coupling devices.

FIG. 16A is a flowchart representing a method of making one or more coupling devices conforming to a standard according to embodiments of the disclosed subject matter.

FIG. 16B is a flowchart representing a method of using one or more coupling devices that conform to a standard according to embodiments of the disclosed subject matter.

FIGS. 17A and 17B illustrate an alternative configuration of a connector to illustrate additional embodiments.

DETAILED DESCRIPTION OF THE EMBODIMENTS

Figure 2A:
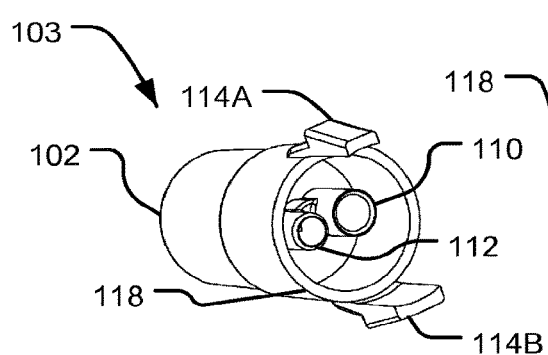
FIGS. 2A through 2D show an embodiment of a coupling assembly of an asymmetric design that can be made from a two-part single action molding.
Figure 2B:
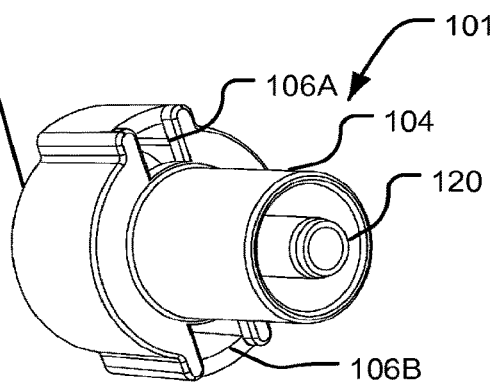
Figure 2C:
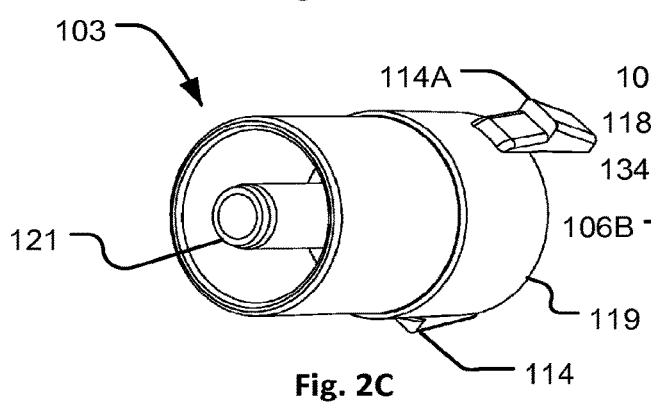
Figure 2D:
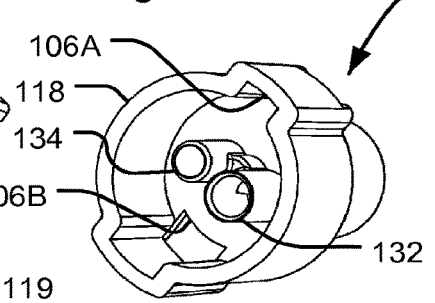

Referring to FIG. 1A, first and second coupling devices 1A and 1B each include a Y-junction 12A and 12B which join respective male 16A, 16B and female 15A, 15B connectors to a respective common line 10A, 10B. Each coupling device 1A, 1B has an interfering element 18A, 18B. Referring to FIG. 1B, when the coupling devices 1A and 1B are properly mated, each male connector 16A and 15B forms a seal with a corresponding female connector 15A, 16B. As shown in FIG. 1C, if an attempt is made to mate the female connector 15A of one coupling device 1A with male connector 15B of another 1B, fluid will leak from the uncoupled pair 15A and 16B there by revealing unsuccessful coupling. Also, the interfering element 18A may interfere with the completing of the connection so that in some configurations with such interfering elements as interfering element 18A, there may be no way even to connect one connector pair such connector 15A with 15B as shown in FIG. 1C.

FIG. 1L shows a modification 17 of the foregoing embodiment in which an annular rim 25 is provided to form a seal with a cap 22 to allow the multiple connector (15A, 16A) arrangement to be sealed. The structure may be packaged as a sterile coupling assembly. Note that in embodiments, the interfering elements 18A, 18B may serve other purposes such as they may serve a shield function or they may provide surfaces to facilitate manipulation.

FIG. 1N is an illustration of an embodiment with mating coupling devices 41B and 41A having mating connectors 4B, 5B, 4A, and 5A that mate, respectively, to form a furcated channel between ports 3A and 3B. In this example, each of the coupling devices 41B and 41A has one each of a male 5A, 5B and female 4A, 4B connector. In the example, the connectors 4B, 5B, 4A, and 5A themselves may be relied upon to engage the coupling devices. Alternatively, non-flow connecting devices may be used to hold the connectors 4B, 5B, 4A, and 5A together. In addition, the number, size, and shapes of the connectors may be used to form mating species of coupling devices.

FIG. 1P is an illustration of an embodiment with mating coupling devices 44B and 44A having mating connectors 6B, 8B, 6A, and 8A that mate, respectively, to form a furcated channel between ports 7A and 7B. In this example, one of the coupling devices 44B has a pair of a male 8B, 6B and the other 44A has a pair of females 6A, 8A. In the example, the connectors 6B, 8B, 6A, 8A themselves may be relied upon to engage the coupling devices. Alternatively, non-flow connecting devices may be used to hold the connectors 4B, 5B, 4A, and 5A together. In addition, the number, size, and shapes of the connectors may be used to form mating species of coupling devices.

FIG. 1Q is an illustration of an embodiment with mating coupling devices 45B and 45A having two male mating connectors 26A that sealingly engage with respective female connectors 26B of coupling device 45A and one female connector 27A that mates with one male connector 27B of coupling device 45B. These form a trifurcated channel between ports 24A and 24B, the lumens of the connectors 26A, 27A being connected to furcating channel 24A and the lumens of the connectors 26B and 27B being connected to furcating channel 24B. In the example, the connectors 24B, 27B, 26A, 27A themselves may be relied upon to engage the coupling devices. Alternatively, non-flow coupling devices may be used to hold the connectors together. Shields or manipulation-enhancing features may also be employed or combined with interference elements. In addition, the number, size, and shapes of the connectors may be used to form selectively interfering engagement elements that define compatible and incompatible species of coupling devices.

In the foregoing, and other examples below, because the misconnected coupling devices have unconnected connectors that constitute major channels, given that each connector may be made responsible for handling half the total maximum flow rate, the incomplete junction is large so that the incompetence of the connection is very obvious. It is therefore unlikely to be overlooked or tolerated by a user or observer. Also, medical devices that detect leaks may have their leak detection mechanisms triggered by improper connection attempts. A drawback of prior art embodiments is that leaks created by misconnection may be substantially smaller than the overall flow so a misconnection may not be so obvious. Thus, in embodiments, a device here can form a connection where interconnected incompatible coupling devices are defined by an open channel that is approximately half the total flow cross-section when properly mated. In trifurcated or N-furcated connectors, the leaking flow may be an even higher fraction of the total, assuming a misconnection is made between only one connector on each end.

Further embodiments may be developed based on the foregoing in which more than two male-female connectors are used in each coupling device. In such embodiments, unsuccessful mating of coupling devices may result in a breach constituting less than half the flow area but at least a substantial fraction of the total flow area. The relative sizes of the male and female connectors may also be varied to create a range of different unique coupling pairs. The relative locations of the male and female connectors may also be varied to create a range of different unique coupling pairs. The shapes of the male and female connectors may also be varied to create a range of different unique coupling pairs. Combinations of these variations can be used to further expand the range of coupling pairs. Still further unique pairs can be generated from interfering and connecting elements such as the shape, position, or size of the interfering elements 18A, 18B.

Note that the interfering elements 18A, 18B may be of a variety of sizes and/or shapes, for example they may wrap at partly around the connectors 16A, 16B, 15A, 15B to act as a partial cover. They may also serve to facilitate handling, and/or provide orienting features to facilitate proper relative orientation of the coupling devices.

A common feature of the foregoing (and many further) embodiments is that the leak path resulting from unsuccessful mating forms part of the normal flow channel when the connection is properly made. In prior art systems, the leak path includes a side channel that is not normally used for flow. This may provide a result that if an improper connection is made then corrected, there is no risk that an unused flow path portion will contain stagnant liquid. Such stagnant pools may create a risk for multiphase flows or biological fluids, such as sedimentation or thrombogenesis. So in embodiments, a two-part coupling device system uses only main channels to provide the compatibility scheme and no side channels are required. This makes for a clean system which is simple and cannot result in side pockets where flow can stagnate.

The features described above are common to the following embodiments below as are the variations attributed to them.

Note that although in the embodiments discussed above and below, the device employed for preventing misconnection may include an interference element, other types of connection prevention devices may also employ, for example, devices that induce excessive friction, such as an invaginating post and recess that fit too tightly to allow the coupling devices to be brought together.

A feature of the foregoing embodiments is that coupling devices for a particular source of fluid or upstream or downstream component can only be mated with a corresponding coupling device. A feature of the embodiments is to prevent a certain coupling device from being connected to any other type of coupling device without rendering the connection essentially useless and further to make it apparent to the user that the connection is not possible or evident that an improper connection is not successful.

In the foregoing, a useful property of a coupling assembly is evident. This is that any attempt to defeat the functionality of the mismatched coupling devices is revealed and rendered useless. Above, a hermaphroditic coupling assembly, each having at least male and a female side, can be mated. If either coupling device is connected to a tube with only a male or female connector, the connection will leak since each side has a Y-branch. Further embodiments can include coupling devices with only males on one side and only females on the other side. Although not illustrated, their configurations should be evident from the disclosure.

Although the embodiments illustrated above provide manufacturing economies in that each member of a mating pair may be identical in configuration and therefore manufacturable from the same mold, it may be desirable to prevent interconnection of one source to another source, for example rather than a source to a sink. In that case, a feature that indicates or prevents identical coupling pairs from being interconnected may be provided. One example is to make the coupling devices non-identical such as by providing incompatible interfering elements or by providing males connectors on one coupling device and female connectors on the other. Another example is to provide interfering elements such as posts (see embodiments infra) on one coupling device for sources and a different set of posts on the other such that when a source to source coupling is attempted, the posts would prevent mating of the coupling devices. Colors and labels may be added to the embodiments to further clarify proper and improper mating pairs.

The foregoing and further embodiments may be provided as parts of tubing sets that are sterilized. They may also be provided with medicaments and medications. For example, a coupling element of a first unique pair may be provided on a medication container port and its complement on an infusion line coupling. A different unique pair may be provided on a medicament container such as a bag of dialysate and its complement on a fluid circuit interoperable with a dialysis treatment device. Another example may be a fluid circuit used for generation of peritoneal dialysate from components in which each component is attachable to respective ports of a manifold by a respective unique pair.

Embodiments may be formed, by suitable arrangement of posts or other interconnection elements, to form universally compatible, or quasi-universally compatible coupling devices. For example, a coupling device with no interfering elements may be mated to ones with different arrangements of interfering elements which render them selective with respect to certain other coupling elements also having interfering elements. Embodiments are discussed below. Such universal coupling devices may be used, for example, on sources of fluid that are not considered risky or harmful. For example, they may be provided on bags of saline whilst more selective coupling devices may be provided on medication containers.

Referring to FIGS. 1D and 1E, coupling devices 30A and 30B, in addition to having pairs of male and female connectors 15A, 15B, 16A, and 16B, also have compatible interfering or engaging element pairs indicated at 32A, 32B and 34A, 34B. When arranged as shown, elements 32A and 32B are positioned so that when the coupling devices 30A and 30B are pushed together, the interfering or engaging element pairs indicated at 32A, 32B and 34A, 34B permit the insertion of male connector 16A into female connector 16B and male connector 15B into female connector 15A. However, a different species indicated at 30C in FIG. 1E has interfering elements 32C and 34C that are do not fit the elements 32B and 34B blocking the insertion of male connectors 16A and 15B into respective female connectors 16B and 15A.

The elements 32C and 32B may interfere to prevent the mating of the connectors 15A, 15B, 16A, and 16B by virtue of their shapes, positions, angles, and/or other aspects that cause them to block full positioning of the coupling devices 30A and 30C that would permit the connectors 15A, 15B, 16A, and 16B from fully mating. By interfering, it is intended to convey that the elements mutually block or deflect. Interfering elements may take the form of functional elements such as sterility shields, manipulations surfaces, or latches that keep coupling devices from coming apart, or other features such as alignment devices or devices that facilitate handling. Interfering elements may constitute separate elements such posts and matching holes. Examples are described below.

It should be emphasized that these illustrations are conceptual and not intended to represent the detailed configuration of an actual commercial embodiment, which details would be possible to provide by those of skill in the art.

The male and female connector elements may be formed such as to form mutually mating or non-mating pairs by virtue of their shape, size, and/or position. For example, in FIG. 1F, male and female connectors 37A, 37B and 35A, 35B are shaped and/or sized so as to be compatible only with coupling devices 31A, 31B that are capable of mating with them and to prevent the complete connection of incompatible species of coupling device. Examples include ellipse-shaped (in cross-section) connectors that may be uniquely compatible by virtue of their orientation as indicated at 43 in FIG. 1L or luer-like connectors with beveled tips as indicated at 42 which, if mis-connected, would leak.

Referring now to FIGS. 1G and 1H, the angular orientation of the pair of mating male and female connectors may specify uniquely compatible pairs of coupling devices. Coupling devices 50 and 51 have male 56A, 56B and female 55A, 55B counterpart connectors that are positioned so as to permit them to engage when shield portions 60A and 60B are oriented for engagement. Latch clips 62A and 62B are also positioned to engage engagement edges (not shown) on the shield portions. Note that coupling device 51 is shown from the back and hidden lines used to show the positions of the male and female connectors 55B and 56B. FIG. 1H shows essentially the same features as in FIG. 1G except that the pair of connectors 72A and 72B of coupling devices 52, 53, while mutually compatible, are not compatible with either of the connectors 55A, 56A and 55B, 56B of FIG. 1G (50 and 51).

Referring now to FIG. 1J, coupling devices 89A, 89B that are similar to those of FIGS. 1G and 1H are shown from a side view. A shield portion 87A, 87B helps to protect connectors 84A, 84B, 86A, 86B from touch contamination and facilitates handling. Coupling device 89A is shown with the shield portion 87A facing the viewer. A tab 85A, 85B interlocks with a respective slot 88A, 88B. Common lines 82A and 82B are connected to, and interconnect, connectors 84A, 84B, 86A, 86B respectively.

FIG. 1K illustrates a mechanism for forming a Y-junction by defining ports 95 at an interface of two cylindrical sections 93 and 91 with one cylindrical section where the latter forms the common line of the Y-j unction and the former form the male and female connectors. The arrangement may be formed by a single action mold. The broken lines 94 indicate a cutout which may be formed in a post-shaped portion of an upper mold to accommodate a cylindrical post shape of the bottom mold.

FIGS. 2A through 2D show an embodiment of a coupling with coupling devices 101 and 103 of an asymmetric design that can be made from a two-part single action molding. Each of the coupling devices 101 and 103 has a respective body 102, 104 with an internal passage that connect connectors 110, 112, 132, and 134 to respective common ports 121 and 120 for connection to a supply or destination line or device. A rim 118, 119 surrounds a respective set of connectors, helps to protect them from touch contamination during use, facilitates handling, and provides engagement for a cover 140 described below. Locking tab 114A can be inserted into, and engage the end of port 106A and locking table 114B can be inserted in, and engage, the end of port 106B. With locking tab 114B being larger, it is not possible to insert it in port 106A. In further embodiments, the angles of the tabs 114A, 114B and corresponding ports 106A and 106B pairs can define features that make for compatible and incompatible coupling device species and compatible and incompatible orientations in the same manner as the diverse locking tab sizes are used here.

Figure 3A:
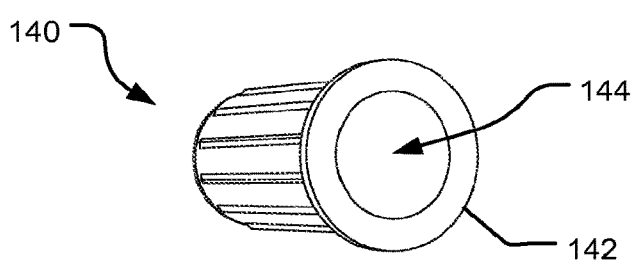
FIGS. 3A through 3C illustrate cap and sealing assemblies that may be used with the configuration of FIGS. 2A through 2D.
Figure 3B:
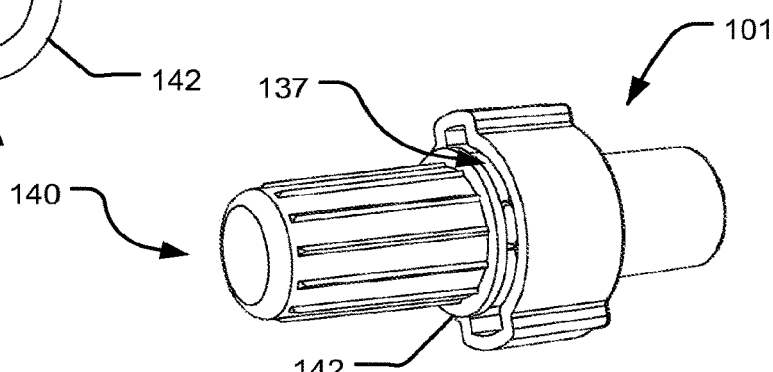
Figure 3C:
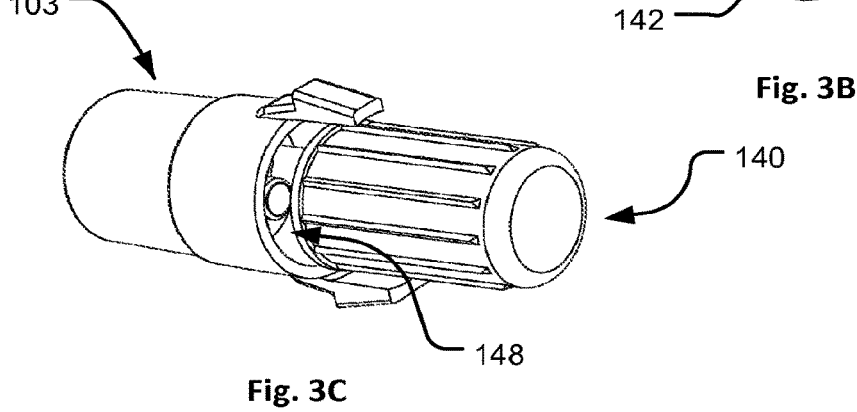

A feature shown in the present embodiment, and which may be applied to other embodiments and variations enabled hereby, connectors 110 and 112 and 132 and 134 may be enclosed in a cover 140 shaped as shown in FIGS. 3A, 3B, and 3C and inserted in a respective well 137, 148. The cover 140 may have a rim 142 and a recess 144 to accommodate the connectors 110 and 112 and 132 and 134. It may be formed by vacuum molding and may have ribs to improve rigidity.

The connectors 110 and 112 and 132 and 134 may be extended into further embodiments by adding features such as described above including variations in number, angle, shape, and/or additional elements such as interfering elements. The coupling devices 101 and 103 are compatible, but it is clear using the toolkit of devices described above and below herein, that variations that are compatible and incompatible are readily possible.

The shape of the structures of the coupling devices 101, 103 are such that, it will be apparent, they may be formed from a single action mold. That is, the shapes of opposite surfaces of each part have neutral or positive draft permitting each entire part to be formed from a single two-part mold without any complex actions. Also, the design has the features discussed above with reference to FIGS. 1A to 1Q or may be readily modified to include them according to the foregoing description.

FIGS. 4A and 4B show an embodiment of a compatible coupling device pair 200. A first coupling device 202 mates with a second coupling device 203. First coupling device 202 has a pair of latching tabs 206 that insert into and latch in ports 208 of the second coupling device 203. Male and female connectors 210 and 212 (not shown for coupling device 202) are positioned within respective annular shields 208, 211 which may receive a cover as described with reference to FIG. 3A. A common port, as indicated at 204, is provided which branches to the male and female connectors 210, 212. FIG. 4A shows the coupling devices far apart and FIG. 4B shows them about to be interconnected. The tabs 206 ensure that once connected the two coupling devices do not come apart inadvertently. They may be disengaged by pressing the tabs 206 inwardly together. Common ports such as indicated at 204 and elsewhere in similar embodiments provides the ability to connect the coupling devices to tubing including plain tubing, parts of fluid circuits, sources of fluid such as containers, and other external devices.

FIG. 4D shows a coupling device 209 with another type of locking system that uses a lock ring 230 that engages internal threads (not visible inside the lock ring 230) with tabs 218. FIG. 4C shows the coupling device 207 without the lock ring 230 to reveal features beneath the lock ring 230. A common port 232 connects internally of a body to male and female connectors 220 and 222. Guides 226 fit in slots 228 to prevent rotation and provide a feature to form selectively compatible pairs (or sets) of coupling devices. Note FIG. 4C shows the coupling device 207 (the one carrying the lock ring 230) without the lock ring 230 to show how the parts engage. In use, the lock ring 230 would be pre-assembled.

FIG. 5A shows first and second coupling devices 302 and 308 each having a pair of male and female connectors 342 and 344. A slot 332 receives a tab 330 and its position relative to the tab 330, with respect to the two connectors 342 and 344, determines whether the coupling device 302 and 308 are compatible. In the illustrated example, the tab 330 is aligned with the slot 332. If the angular placement of the slot 332 and tab 330 are not aligned in a variant of the pictured device pair, when the connectors 342 and 344 are aligned to connect mutually, an interference will arise and the coupling devices 302 and 308 will not come together sufficiently to connect the male and female connectors 342 and 344. The devices use the same locking tab 331 and port 333 feature described above. This locking feature is common to the embodiments of FIGS. 5A through 5F so it will not be described again. However, it will be noted that the locking tab 331A is smaller than locking tab 331B which serves as an orienting mechanism or compatibility-selection mechanism, which may be combined with the tab and slot mechanism to form various species of compatible and incompatible coupling devices.

FIG. 5B shows another pair of coupling devices 304 and 310 with a different form of interference device in the form of posts 322 and 320. The posts, if aligned when the male and female connectors are positioned for connection, may interfere, thereby preventing connection. If one coupling device 304 or 310 is rotated to cause the interfering posts 320 and 322 to avoid each other, then the male and female connectors will be unaligned and connection will again not be possible, even for a species in which the locking tabs 334A were sized to permit the coupling devices 304 and 310 to be so rotated and interconnected. FIG. 5C shows coupling devices 306 and 312 with a tab 326 that fits in a port 324 and otherwise interferes with other parts of the coupling device 306 if not aligned with the port.

FIGS. 5D and 5E illustrate coupling devices 350, 352, and 354 which are incompatible, respectively, with coupling devices 351, 353, and 355 by virtue of having interfering elements as described now. In the pair 350 and 351 of FIG. 5D, the position of posts 356 and 358 prevent closure of the coupling device pair. These posts may be placed in a variety of positions on the surface 357 to form other embodiments and may number, and be sized, variously to form ranges of compatible and incompatible species. In the pair 352 and 353 of FIG. 6B, the position of posts 362 and 364 and/or 366 and 368 prevent or permit closure of the coupling device pair. FIG. 5F illustrates a compatible pair of coupling devices 354 and 355. It has interference devices that are arranged so as not to interfere with each other but would interfere with coupling devices having different arrangements of similar features. Coupling devices 354 and 355 may be modified to form various combination of posts 372 and raised surfaces 374 which may be positioned at different positions to form a variety of compatible and incompatible (mating and non-mating) pairs.

Note that it may be confirmed by inspection that the foregoing embodiments may be molded using a simple two-part mold. In embodiments, this is the case, but it is by no means essential to the disclosed subject matter.

Figure 6:
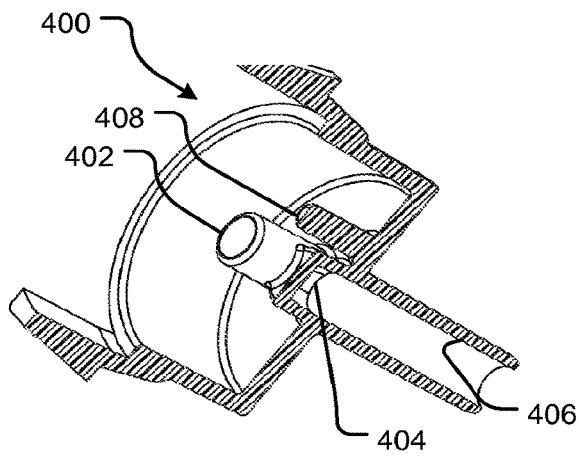
FIG. 6 shows a section of a coupling device to illustrate how the Y junction may be formed with a two-part molding process in a coupling device arrangement.

FIG. 6 shows, in a coupling device embodiment 400, a feature discussed above in which a Y-junction is formed by the volumetric overlap of the lumens 406, 402 of the common line 406 and mating connectors (one of which is indicated at 402). This forms a junction (or port) 404 between the connectors (e.g., 402) and the common line 406. The configuration lends itself to being formed by two-part mold. The figure also illustrates how a post 408 can be provided in a similar molding operation as it should be clear the shape is characterized by neutral or positive draft surfaces.

Figure 7C:
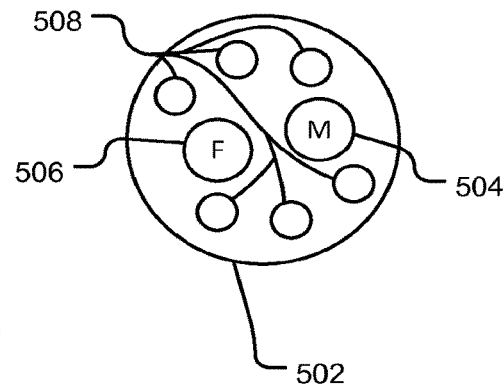
FIG. 7C illustrates a scheme that may be used with all the disclosed embodiments for forming compatible and incompatible sets of coupling devices.
Figure 7A:
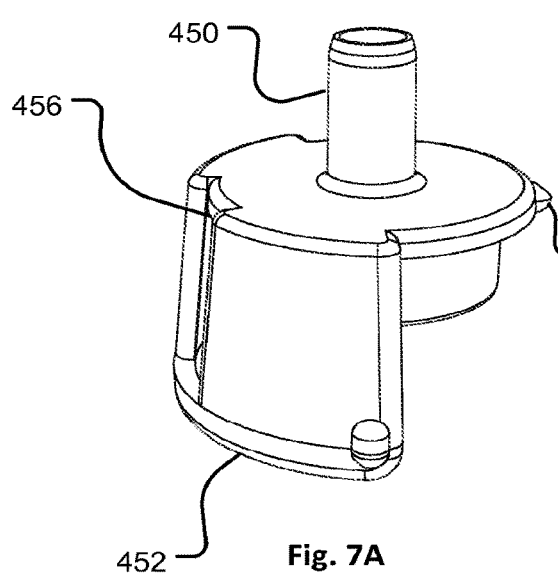
FIGS. 7A and 7B show details of a symmetric embodiment with locking and protection features.
Figure 7B:
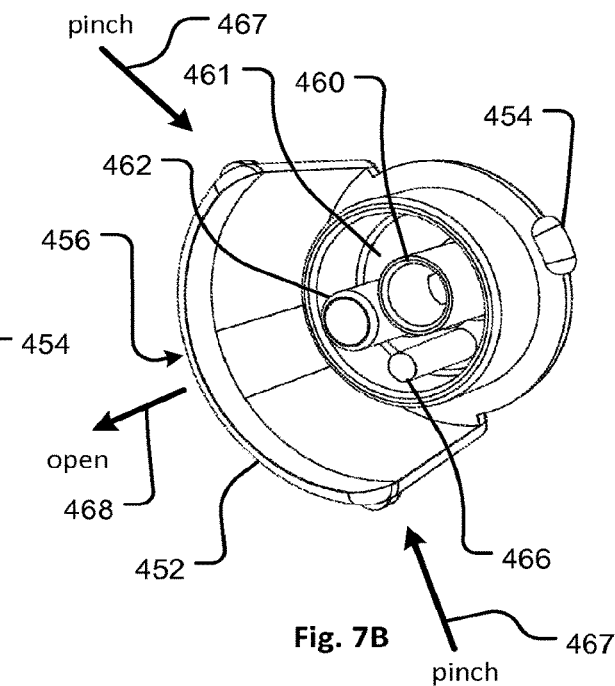

FIGS. 7A and 7B show a coupling device that has a symmetrical shape so that a mating pair can be formed from a single mold. The two coupling devices interlock by means of a tab 454 that engages an edge 456 when the male and female 462 and 460 connectors are brought together sufficiently to seal. A shield 452 can be pinched as indicated by arrows at 467 to flex the shield 452 moving the edge 456 radially outward (see arrow 468) thereby releasing the tab 454. A common port is shown at 450. In further symmetrical embodiments, a post 466 can be positioned varying positions to form compatible and incompatible sets of coupling devices. The symmetrical devices would always be compatible because they are mirror images of each other, but the variants would not necessarily by compatible with each other.

FIG. 7C shows a scheme for arranging the post 466 and additional posts to create varying embodiments. The possible post positions are indicated at 508. Different species of coupling device may have a different combination and number of posts at these locations. Even with the unnecessarily restrictive assumption that posts at 508 (corresponding for example to the post 466 but applicable to other embodiments disclosed herein) may only have the six indicated positions around the male 504 and female 506 connectors on a coupling device 502, it is possible to form a large number of arrangements. And further assuming the posts 508 have a single length and size, a coupling device with one post 508, would still be able to mate with many other coupling devices with posts and multiples of posts in the other 5 non-interfering locations (including the one with zero posts). By varying the lengths and sizes of the posts or providing other numbers, much larger sets are possible. This will be apparent from the discussion of FIGS. 15A through 15E.

Thus, it will be observed that even with a simple scheme as illustrated in FIG. 7C, a very large number of combinations and compatible sets may be formed. By combining with other features such as size and angle of locking tabs and further interference devices such a connector spacing, size shape and the other features described herein, a great variety of coupling device species are possible. Note that although the simple diversification scheme describe above was applied using the basic design of FIGS. 7A and 7B, it is clearly applicable to other embodiments described herein. The scheme can be generalized for other pairs directly. The scheme is elaborated further below, with reference to FIGS. 15A through 15E.

Figure 7D:
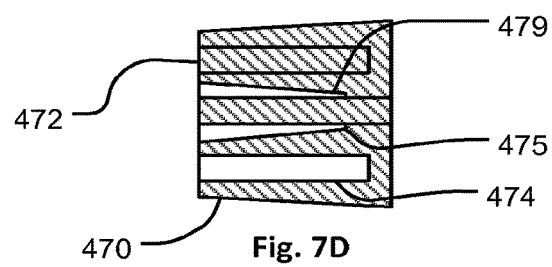
FIG. 7D shows a molding concept for making various species from common elements.

The post scheme described with reference to FIG. 7C may be used with replaceable inserts in a standard mold which inserts are readily machinable (See also FIG. 7D and attending discussion). For example the floor 461 and posts (posts) 266, 508 may be molded with a mold portion 470 that contains holes 474 that may be fitted with inserts 472, or left open as shown at 474, to cause one or more posts to be created in selected positions. A pin 475 is shown in a well portion 479 that forms the connector part 462 in this embodiment. The drawing of FIG. 7D is not detailed and is only for purposes of illustrating the molding concept. This concept is applicable to other embodiments described herein and may be extended other types of interference devices of different shape and description as described herein.

In any of the foregoing embodiments, instead of posts on a planar surface, as illustrated for example in FIG. 7C, the planar surface may be made irregular thereby creating the effect of a variety of posts with selective interfering potential.

Figure 8:
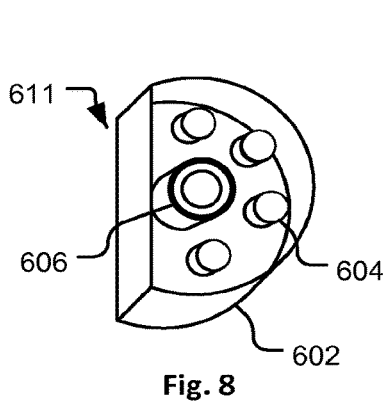
FIG. 8 shows a coupling device that uses an orientating enforcement mechanism to provide a capability of forming a variety of species of coupling devices.

FIG. 8 shows a coupling device 611 with a mechanical feature that enforces a predefined orientation (prevents improper orientation) by having a rotationally asymmetric sleeve part 602 that closely conforms to a similarly shaped insert part (not shown) of a mating coupling device. The predefined orientation ensures that posts 604 (not all numbered but any number may be present) interfere with corresponding opposing posts or posts on the mating coupling device. A connector 606 mates with a suitable connector (not shown) on the mating coupling device.

FIG. 8 illustrates that although it is possible to form alternative orientation enforcement mechanisms, the furcation mechanism has the advantage that it cannot easily be defeated by commonly available rogue connections such a tube end that could be slipped over the sleeve part 602. A user would find it difficult to engage multiple connectors of a coupling device according to the disclosed embodiments.

Figure 9:
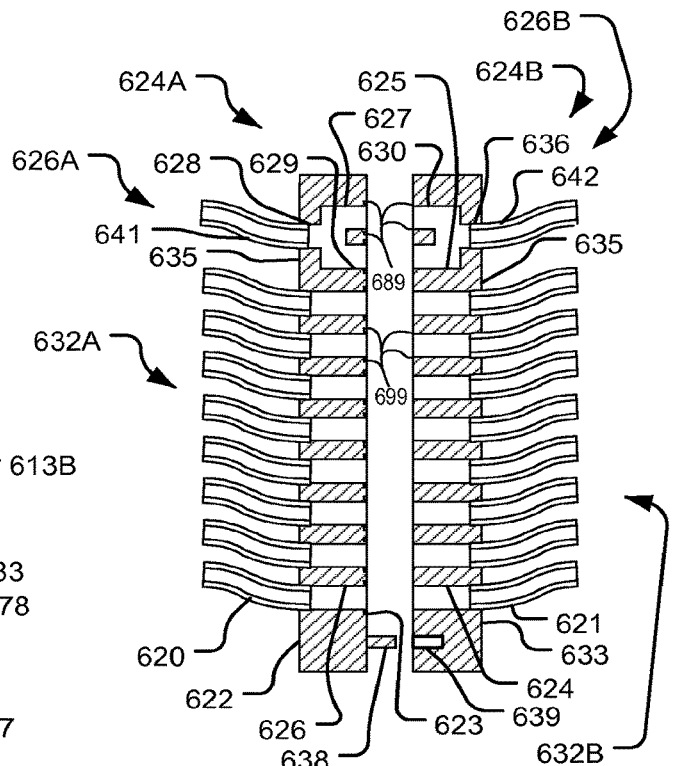
FIG. 9 shows a ganged coupling device pair with a minimum of one n-furcated coupling device portion and an interference feature.

FIG. 9 shows a ganged coupling device pair 624A and 624B with first and second coupling device bodies 622 and 633 with non-furcating channels 626 and 624 (and others as shown) leading to respective connectors (e.g., 699), and furcating channels 628 and 636 leading to connectors (e.g., 689) at the opening ends of furcated channels 625, 630, 627, and 629, respectively. All of the connectors 689, 699 may be identical and formed, for example, by elastomer sealing rings or O-rings with mating faces. Note that only one set of non-furcating channels 624 and 626 is labeled to avoid crowding the drawing, but others are represented. The furcating and non-furcating channels define furcating coupling devices 626A and 626B that are integrated in the ganged coupling devices 624A and 624B, as well as non-furcating coupling devices 632A and 632B also integrated in the ganged coupling devices 624A and 624B. The number of furcating coupling devices and non-furcating coupling devices may be varied to form additional embodiments. For example, a ganged coupling device can include exclusively furcating coupling devices or any ratio of furcating and non-furcating coupling devices. A distinctive feature of embodiments is that there is at least one furcating coupling device in a ganged coupling device pair 624A and 624B. Alternative, as explained below with reference to FIGS. 14A and 14B, one of the ganged coupling devices may carry one or more coupling devices which has a closure rather than a furcating channel. This is an alternative extension of the disclosed subject matter that is elaborated in the discussion of FIGS. 14A and 14B, infra.

The connectors 689, 699 may be sealed by O-rings 623 or other suitable elastomeric seals that are compressed by a suitable latching mechanism (not shown). Of course any suitable connector type can be substituted including any of the types described in embodiments of the present disclosure. Each non-furcating channel 624 and 626 may be connected to a respective tube 620, 621 or to some other fluid circuit system such as a panel-type cartridge fluid circuit (not shown). Similarly, furcating channels 628, 636 may connect to respective tubes or to some other fluid circuit system such as a panel-type cartridge fluid circuit (not shown). An interference device capable of ensuring against misconnection of incompatible species of ganged coupling devices may be provided on the ganged coupling device pair, such as an arrangement of one or posts (one shown at 638) on one of the ganged and one or more corresponding recesses (one shown at 639). As in previous embodiments, the interfering devices may take a variety of forms and may be arrayed in a variety of patterns or positions to produce compatible and incompatible families of ganged coupling device species.

Figure 10:
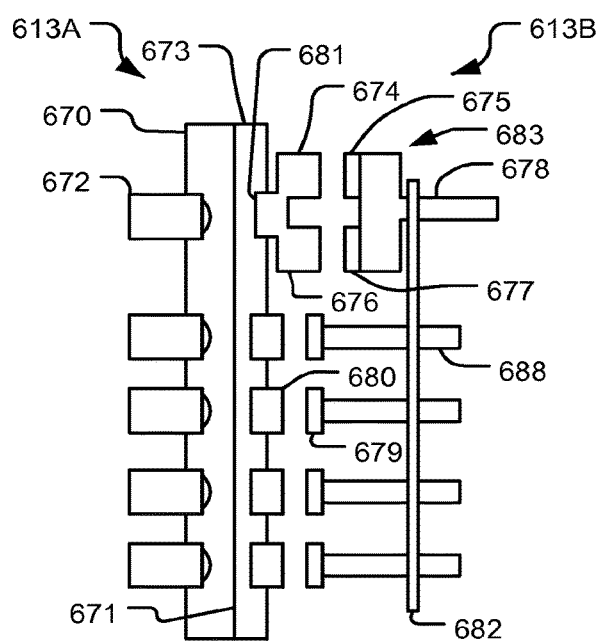
FIG. 10 shows a manifold apparatus incorporating a coupling device and other features according to embodiments of the disclosed subject matter.

FIG. 10 shows a manifold device 613A and a manifold coupling device 613B. The manifold device 613A has multiple-connector chamber 673 which fluidly couple the ends of connectors, for example connectors 674, 676, and 680, in a single channel to form a manifold. The connectors 674, 676, and 680 are depicted figuratively and any suitable type can be used. In a practical system, the manifold 673 may be coupled to an actuator mechanism 670 with plungers 672 to that selectively open and close the connector ends by pushing against parts of a membrane 671 abutting the respective connectors, for example at a rear facing port as indicated for example at 681. Connectors 674 and 676 are furcated and combine or divide the flow through a port 681, depending on the flow direction. The connectors 674 and 676 form a coupling device that interconnects with a furcating coupling device 683 having connector 675 and 677 which lead to a furcating channel 678. The non-furcating connectors 679 and 680 (again only one labeled because they are all identical) lead to respective non-furcating channels, one indicated at 688. The channels and connectors of the manifold coupling device may be interconnected by a member 682 that permanently attaches the connectors and coupling elements together as a unit. The manifold coupling device 613B and manifold device 613A may be made modified in various ways to form selective species of pairs of such devices according to any of the methods or configurations described herein and variations thereof. For example, the furcating coupling device 683 may be provided with interfering elements as described elsewhere herein. Also interfering elements may be provided on the member 682 and manifold device 613A, for example as illustrated with respect to FIG. 9.

The manifold coupling device may be provided as a unitary device. This makes the full set of connectors and coupling devices for all connections conveniently available as a unit, thereby discouraging misconnection as long as furcating coupling device 683 is compatible. The member 682 may be configured as a rigid frame such that connectors may only be attached when the furcating coupling device 683 is in a in a predefined orientation with respect to the connectors 674, 676. Then all the connectors 679 are positioned, as a result of orienting the member 682, to mate with corresponding connectors 680, so that the selectivity of the coupling device 683 may ensure the other connectors are properly mated. In various embodiments based on the embodiment of FIG. 10, the number of furcating and non-furcating coupling devices may vary and any number of each may be included. Also, the variation described with reference to FIGS. 14A and 14B may be utilized to form further embodiments.

Figure 11A:
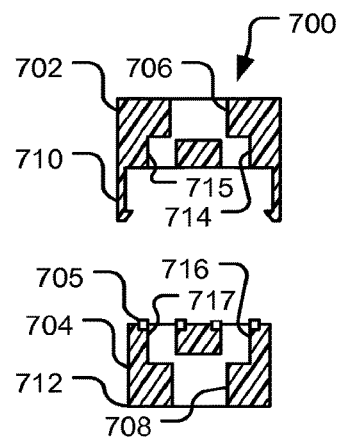
FIGS. 11A and 11B illustrate the fact that various types of connectors may be used to exploit the disclosed subject matter and form various embodiments.
Figure 11B:
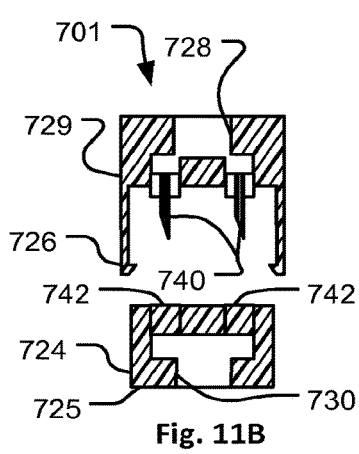

FIG. 11A shows a coupling device 700 that employs butt-sealing type connectors. A body 702 provides furcating channel 706 on one side and another body 704 provides a furcating channel 708 on the other side. Connector 715 seals to connector 717 using elastomeric seals 705 (only one labeled) when the two bodies 702 and 704 are urged together and clipped in place by latches 710 which engage on edges 712 of the body 704. Of course the elastomer seals may be relocated to the other or a combination of the blocks 702 and 704 in additional embodiments. To illustrate further that a variety of different types of connectors may be used to achieve various functions of the disclosed subject matter, another type of connector is illustrated which employs needles 740 and septums 742. A body 729 provides furcating channel 728 on one side and another body 724 provides a furcating channel 730 on the other side. Each connector with a septum 742 seals to a connector with a respective needle 740 when the two bodies 729 and 724 are urged together and clipped in place by latches 726 which engage on edges 725 of the body 724. Of course the needles and septums may be relocated to the other or a combination of the blocks 729 and 724 in additional embodiments.

Referring now to FIGS. 12A and 12B, first and second coupling devices 603A and 603B mated to each other. The first coupling device 603A has a body 644 with a flow channel 646 that furcates into channels 648 and 651. The second coupling device has a body 647 with a flow channel 649 that furcates into channels 650 and 652. Respective connections may be made to channels 649 and 646. The body 644 of the coupling device 603A may be seated in a well 631 to seal openings of channel 648 to channel 650 and an opening of channel 651 to channel 652 creating a flow path between the channels 646 and 649. An aperture 653 helps to ensure that an improper connection will leak fluid and may provide an access for molding elements that may be used to form channels 650 and 652. Referring now also to FIG. 12C, a view taken about planes A-A indicated at 780 and B-B indicated at 781 show how the coupling device 603A may be provided with features such as grooves 754 and ridges 756 to create a scheme for forming species pairs that may be mated and species that cannot mate with them by varying the positions, sizes, shapes of ridges and grooves that are compatible and incompatible depending on the species.

FIG. 13 illustrates a pair of coupling devices 800A and 800B that are capable of mating and in which magnetic attraction of magnetic blocks 812 and 822 are used to force together connectors 818 and 814 respectively with connectors 820 and 826. In the present embodiment, a single elastomeric seal 824 in block 822 engages a complementary groove 816 in block 812 to form a seal that surrounds both connector pairs 818, 814 and 820, 826. Arrangements of posts 828 and wells 829, for example, or other interfering elements may be used to form species that can mate and ones that cannot mate using features and teachings from the other embodiments. Also, the shapes of the seals may be varied according to different patterns to form another mechanism, which also may be applied to other embodiments, to form additional species that can mate or which are unable to mate. Thus, where seals are shaped such that they cannot align, the result will be a leak indicating the incompatibility of the coupling devices.

FIGS. 14A and 14B show an alternative scheme that may be used to form various species of coupling devices. The teachings with regard to all of the above embodiments may be applied in a scheme in which, rather than providing a first coupling device that furcates an internal channel thereof, and mating it to one that also has a furcating channel, one coupling device would contain a single channel and connector and a device to close one of the connectors (or other type of opening). A first coupling device 870A with a body 840 contains a single channel 844 with an elastomer-type butt connector 849 at the end thereof. The first coupling device body 840 also has a plug 848. A second coupling device 870B with body 842 has a channel 846 that furcates into two channels 852 and 854 with respective connectors constituted by the respective openings thereof at 856 and 858. One of these channels 858 is sealed by the connector 849 when the coupling devices 870A and 870B are interconnected as shown in FIG. 14B. The other opening 856 is closed by the plug 848. A suitable latching mechanism may be provided to hold and urge the bodies 840 and 842 together. By this scheme, a function that is similar to that of the other embodiments may be created. The scheme may employ coupling device embodiments that are mechanically similar to the embodiments disclosed. A variety of embodiments may be envisioned as modification of the previously disclosed embodiments with one (or more depending on the number of connectors) of the furcating channels of one connector completely filled in. Of course the coupling devices would not necessarily be manufactured that way. Thus, it is proposed that the concept behind the embodiment of coupling devices 870A, 870B provides a prescription for modifying any of the foregoing embodiments to form new embodiments.

FIGS. 14C and 14D show embodiments in which a coupling device has two channels that connect to a single channel forming a double-to-single channel coupling device. Referring to FIG. 14C, a first female coupling device has body 1002 with a single channel shown at 1010 that receives a male coupling device body 1006 with two channels 1007. The single channel 1010 is shaped according to the outer surface of the male body 1006 over a portion thereof at least, for form a seal with the male coupling device body 1006. Thus, the two channels 1007 are connected by a single channel 1010 upon connection of the coupling device. The connection concept embodied in the coupling device arrangement may adapted for use in coupling device described elsewhere herein to form new embodiments.

Referring to FIG. 14D, a second female coupling device has body 1012 with a single channel shown at 1011 that receives a male coupling device body 1005 with two channels 1009. The single channel 1011 is shaped according to the outer surface of the male body 1005 over a portion thereof at least, for form a seal with the male coupling device body 1005. Thus, the two channels 1009 are connected by a single channel 1010 upon connection of the coupling device. The connection concept embodied in the coupling device arrangement may adapted for use in coupling device described elsewhere herein to form new embodiments.

It will be apparent that the female body channel must provide a conforming shape to prevent a leak from either of the male body channels in the embodiments of FIGS. 14C and 14D. This feature discourages the use of connectors such luers or even plain tubing ends being connected inadvertently.

Figures 15A, 15B, 17A, 17B:
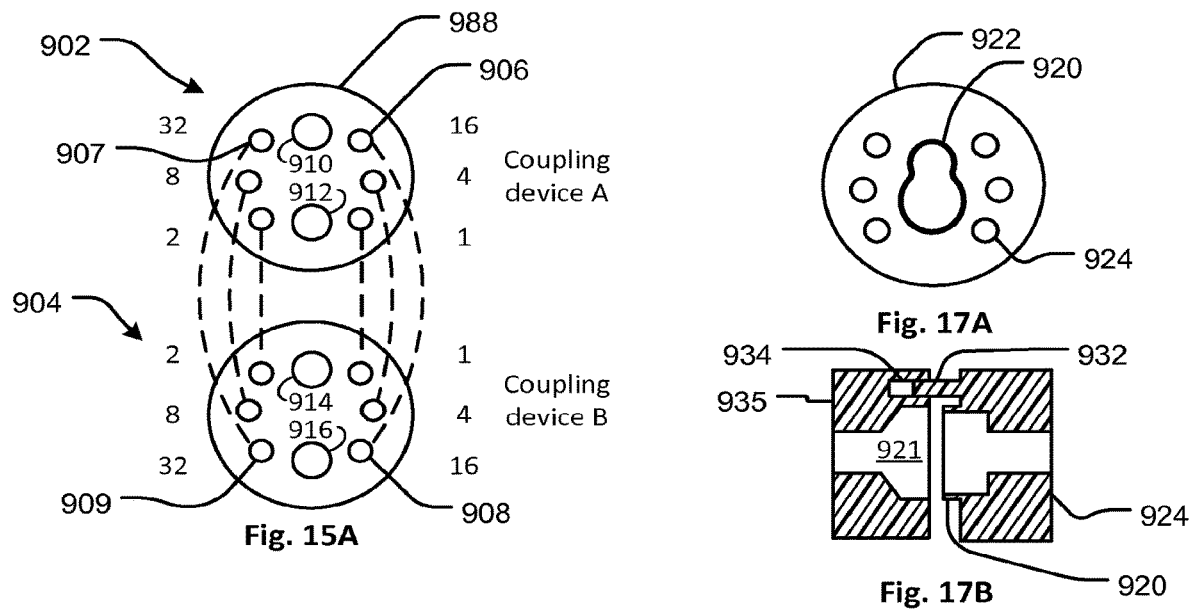

Referring now to FIGS. 15A through 15E, as discussed above with reference to FIG. 7C, disclosed embodiments provide a basis for making a variety of compatible and incompatible species of coupling device. FIG. 15A shows a pair of coupling devices 902 and 904. Coupling device 902 has a pair of flow connectors 910 and 912 and coupling device 904 has a pair of flow connectors 914 and 916. Each coupling device 902 and 904 shows standardized locations of posts 906, 907, 908, and 909 (not all six locations on each coupling device is shown to avoid crowding the drawing). There are six locations at different points on a face of each coupling device. When the coupling device 902 is mated to the coupling device 904, the two faces shown in the drawing, face each other. Therefore, any posts at identical locations will interfere and block the ability of a user to make a connection between the respective connectors 914 to 912 and 916 to 910. The posts may be labeled according to a binary scheme as 1, 2, 4, 8, 16, and 32 which are shown on the drawing. The binary scheme allows a binary number to be used to represent the post layout in a single table shown in FIGS. 15B through 15E (the table is broken into quadrants to make it legible) to indicate combinations of post positions that form compatible and incompatible species of coupling device. Again, a compatible species of coupling device is a pair that can be successfully connected for fluid flow. If posts are in interfering positions on two example coupling devices, the two are not compatible because the interfering positions prevents their interconnection.

In an example, assume coupling device A has two posts located locations 906 and 907 and coupling device B has two posts located at locations 908 and 909. And assume that no posts are present at the other locations. Both arrangements would have posts at the 16 and 32 locations which corresponds to the binary number 110000 (i.e., 32+16=48=110000 binary). The combination of layouts:

coupling device A uses 110000 (posts at locations 16 and 32)

coupling device B uses 110000 (posts at locations 16 and 32)

is shown in Table 15E. As will be confirmed by inspection, the posts in this example would be directly opposite each other and therefore would interfere making the pair of coupling devices incompatible. Table 15E represents the conflict with X (circle in Table 15E). On the other hand, if coupling device A has posts located at positions 1, 2, 4, and 8 and the other coupling device has posts at locations 16 and 32, then no interference occurs. In this pair, coupling device A is represented by 15 or 001111 binary and coupling device B by 48 or binary 110000. This combination is shown in the table of FIG. 15D in the circle superposed thereon. There is no X at this location, indicating the combination of coupling devices is compatible.

Note the features described with reference to FIGS. 15A through 15E are readily applied or extended to other embodiments herein and are clearly not limited to the particular shape and configuration of the coupling device represented in FIG. 15A. Also, the design of the coupling devices, to the extent illustrated FIG. 15A is symmetrical. It should be readily apparent that the scheme is not limited to symmetrical coupling device configurations, for example it may be applied to the embodiment of FIG. 5A.

In all the embodiments and in further embodiments falling within the scope of the disclosed subject matter, it may be desirable for the coupling devices to be configured so as to make it easy for a user to identify compatible and incompatible coupling devices easily and without close inspection. Thus, one or more distinct features which make it evident whether a coupling device conforms to a standard specification for the coupling device and which coupling devices are compatible, would be desirable. There are many known ways for providing such indications, for example, a standard set of color-coding may be used. Labeling the coupling devices by means of tags with specific shapes may also be used. The coupling devices may be labeled using protective caps or seals, which may have embossed codes or color coding, for example. An example is the cover 140 shown in FIG. 3A.

As indicated above, it will be noted that the schemes described above and others that may be generated based on the present disclosure, provides for the making of families of compatible and incompatible coupling devices. These "prescriptions" may be used to establish a standard for allowed coupling devices based on defined classes of devices to which the coupling devices will be attached. For example, the standard might define a class of containers of dialysate. The standard may specify that all coupling devices attached to containers of dialysate use a specific coupling device embodiment, for example, a predefined arrangement of posts such as one of the specific examples described above with reference to FIGS. 15A through 15E (and indicated by circles in the respective tables). The article would have distinct features to indicate the type of coupling device and/or the class of article to which it is coupled and such features may also be part of the standard and specified by the standard data. The presently disclosed subject matter lends itself to such a standard not only by providing ways to manufacture large families of alternative configurations that are compatible and incompatible but also by providing a connector configuration, for example, the multiple connector configuration, which may be unique. This unique configuration, by its shape is difficult to connect to known coupling devices. Thus, it will be evident that coupling devices not conforming to the standard will almost certainly be incompatible with the coupling devices defined by such a standard and employing the coupling device configurations of the presently disclosed subject matter.

Note that in additional embodiments, the locations such as 908 may identify posts on one coupling device and recesses that allow the post-bearing coupling device to pass in thereby permitting two coupling devices to mate. So compatible coupling device pairs would have recesses that coincide with any posts and incompatible coupling devices would not have coinciding with all of the posts so that the coupling devices cannot be interconnected.

Referring to FIG. 16A, a process is illustrated for manufacturing coupling devices according to a shared standard. At S10, a manufacturer of coupling devices consults a standard specification representing how to make conforming devices and the various classes of application, namely, the type of article, device, or system to which the coupling devices may be attached. At S12 the manufacturer may identify the class of application for the coupling devices to be manufactured. For example, the manufacturer may be one who makes coupling devices for customer manufacturers who incorporate the coupling devices in their respective articles, devices, or systems. The manufacturer also may be one who makes a device, article, or system with an integrated coupling device. At S14, the description of the conforming coupling device is identified responsively to the class in accord with the standard specification. At S16, the manufacturer may configure a manufacturing process to make one or more coupling devices and/or articles, devices, or systems with attached coupling devices, according to the indicated conforming description. At S18, the coupling device is manufactured, which may include the manufacture of the article, device, or system.

Examples of articles, devices, and systems include containers (filled with a particular type of fluid and unfilled), a disposable fluid circuit for a medical treatment, a water treatment plant (which may have a coupling device for product water); a needle set, a pressurized air hose, an online dialysate preparation plant, or a filter.

Referring to FIG. 16B, a user may provide a coupling device or multiple coupling devices as a kit, as part of a system, or integrated in a device at S22. For example, the user could be a dialysis nurse who provides and sets up a fluid circuit and fluids for a treatment. A fluid circuit and fluid packaging may be provided that have pre-attached coupling devices conforming to a standard specification. A purchasing agent may choose to purchase and supply to the dialysis nurse only fluid circuit and fluids that conform to the standard. At S24, a first coupling device is selected for connection. For example, the nurse in the example may install a fluid circuit on a dialysis machine and identify one or more coupling devices to be coupled with other coupling devices. For example, the first coupling device may be attached to a filter which is to be coupled to a fluid circuit coupling device. At S26, a second coupling device is identified and at S28 the coupling devices are coupled. This may be repeated by a user several times.

FIGS. 17A and 17B illustrate an alternative configuration of a connector to illustrate additional embodiments of coupling devices. A coupling device 922, shown facing the viewer in the manner of FIGS. 7C and 15A, has an array of interfering elements 924 that may be positioned in various ways as described with reference to FIGS. 7C and 15A. The embodiment of FIG. 17A differs from the foregoing in that instead of multiple connectors 914, 916 or 910, 912, a single non-rotationally symmetric connector that enforces a predefined orientation (i.e., the connector can only be connected when the mating connector parts are oriented at a predefined angle), is used instead. Here a peanut shaped tubular extension forming a male connector 920 is shown on the face of a coupling device 922 that is otherwise similar to embodiments described with reference to FIG. 7C and FIG. 15A. The peanut shaped male connector 920 fits into a female connector 921 with a body 935. The male and female connectors 920 and 921 may have the peanut shape shown in FIG. 17A. Other embodiments may have any kind of non-round connector and may including butt-type connectors instead of male and female type connectors. Thus embodiments may have any of a variety of shapes that may restrict the ranges of orientations at which the coupling devices may be coupled. An interfering element 932 in the form of a post is shown which fits in a recess 934. One or more interfering elements and/or holes may be arranged to form various compatible and incompatible embodiments as described elsewhere. It should be clear that many of the functions of the multiple connector embodiments may be provided by the single non-round connector embodiment and embodiments derived therefrom that also have single connectors.

Figure 18A:
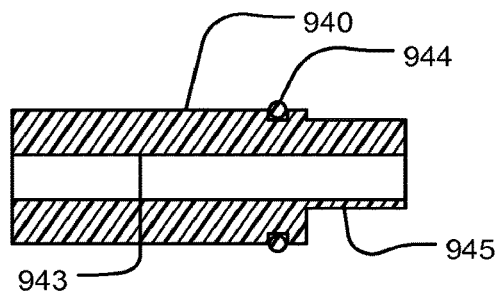
FIGS. 18A through 18H describe a connector embodiment and its use in further embodiments of coupling devices.
Figures 18B, 18C:
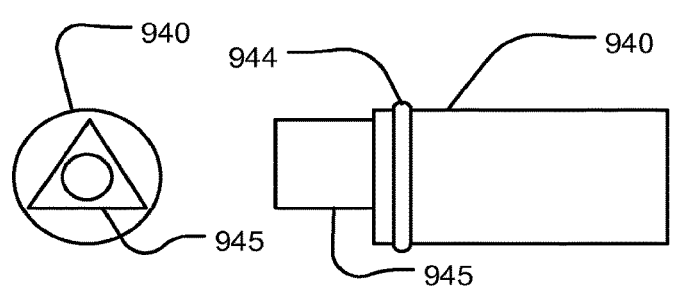
Figure 18D:
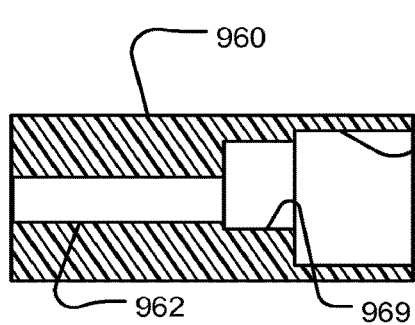
Figure 18E:
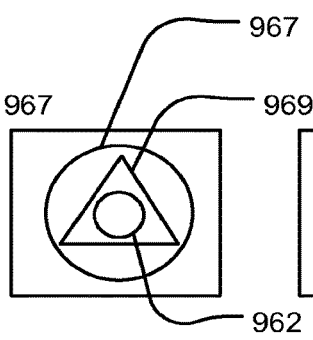
Figure 18F:
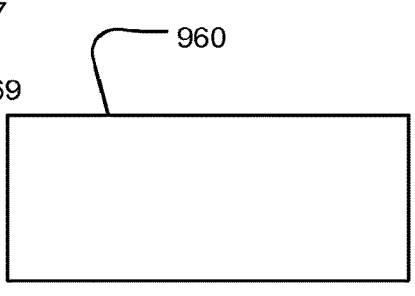
Figure 18G:
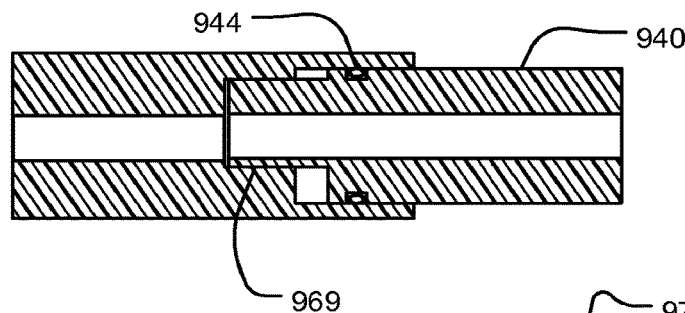

Referring now to FIGS. 18A through 18H, an embodiment of a connector pair is shown with a male connector shown at 940 and a female connector at 960. The male connector 940 has a shaped distal portion 945, illustrated here by a triangle but other shapes could be used in different embodiments. The body 940 is round. An O-ring 944 on the body 940 provides a seal with a round opening 967 in the female connector 960. The shaped distal portion 945 fits in a correspondingly shaped channel 969. The shaped channel 969 and shaped distal portion 945 may ensure that embodiments distal portions of other shapes cannot enter the channel 969. As a result, such embodiments cannot form a seal as shown in FIG. 18G. The male connector 940 has a lumen 943 therein and the female connector has a lumen 962 therein. Once inserted to form a seal, the male connector lumen communicates with the female connector lumen 962 to form a sealed flow path.

Figure 18H:
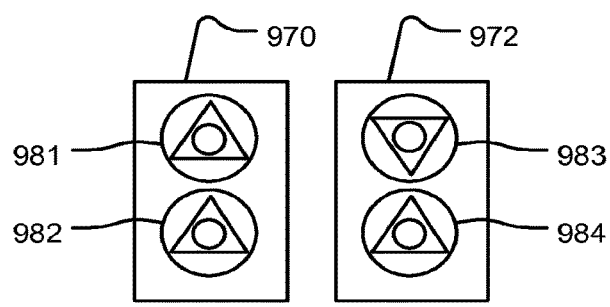

Referring to FIG. 18H, the connector embodiment of FIGS. 18A through 18G and similar variants thereof may be used to form additional ranges of interfering elements in the form of the shapes of the shaped distal portions. The disclosed embodiment of FIGS. 18A through 18G may form a basis for forming further coupling embodiments, for example, ones with multiple connectors as shown in FIG. 18H at 970 and 972. At 970, a coupling device has connectors 981 and 982 that form a first angular relationship with respect to the shaped distal ends and a coupling device has connectors 983 and 984 that form a second angular relationship with respect to the shaped distal ends. Thus, coupling device 972 would not be compatible with coupling device 970. If the angles of the connectors matched, they would be compatible. The foregoing feature may be combined with other interfering element schemes to form extended schemes that combine the interference effects. Alternative variants of the features of FIGS. 18A through 18H include placing the shaped portion proximal of the sealing part on the male connector 940.

In embodiments, the effectiveness of the coupling device selection enforcement and the inhibition of a circumvention of the enforcement mechanism by a user are enhanced by the fact that the multiple connectors require that a certain mutual orientation of the connectors is required in order to create a complete and non-leaking connection. To make a complete connection, for example by making the connection of the male of the first connector to the female of the other while simultaneously making the connection of the female of the first connector to the male of the other requires the coupling devices be mutually oriented with respect to each other. By ensuring this orientation, it is possible to provide an array of interference members that can provide various types of selectivity between connectors of different configuration. This is because the interfering elements can be located at selected points that are sure to come into interfering engagement as a result of the requirement that the coupling devices are properly oriented. Also, as mentioned, by using the coupling device of the disclosed subject matter, the use of a single simple tubular device or soft plastic tube end is difficult or impossible to be used to make a sealing engagement with the coupling device.

Further embodiments and variations are described below and in the claims.

According to embodiments, the disclosed subject matter includes a method of ensuring against improper interconnection of fluid lines. The method includes providing a kit including devices with channels that convey fluid and coupling devices for interconnecting the channels. The method further includes orienting at least some of the coupling devices in such a way as to sealingly engage multiple connectors of each coupling device pair such that which when connected each coupling device pair divides a flow through a respective coupling device and reunites the flow at an end of the respective coupling device pair, the arrangement of the connectors being such as to limit the possible orientations of the coupling devices with respect to coupling devices to which they interconnect. Alternatively the attachment of connectors may block the flow through one of the connectors of the connected coupling device to prevent it from leaking. The number of connectors may vary so other embodiments may have N connectors with a flow that potentially divided into N subflows that are either blocked or combined or even a combination thereof by suitable compatible connectors.

The orienting may include positioning interfering elements of each coupling device pair such that the members of the coupling device pair can be brought together, without mutual interference of the interfering elements, when the multiple connectors of each coupling device pair are sealingly engaged. The orienting may include aligning the axes of each member of a coupling device pair so that they are parallel. The aligning positions the multiple connectors of each coupling device on respective common axes thereof. The providing may include providing multiple coupling devices having interfering elements of the coupling devices arranged such that orienting respective pairs of the coupling devices to sealingly engage their connectors results in mutual interference of the coupling devices, which prevents their interconnection. The orienting may include positioning interfering elements of certain coupling device pair such that they interfere when the multiple connectors of each coupling device pair are positioned with their respective axes aligned so as to be capable of sealingly engaging each other, thereby preventing interconnection of said certain coupling device pairs.

According to embodiments, the disclosed subject matter includes a fluid channel coupling system with coupling devices, each having connectors that sealingly engage corresponding connectors on the other of the coupling devices. Each of the coupling device connectors is in fluid communication with a common port such that when the connectors of two coupling devices are mutually engaged, the respective ports are in fluid communication with each other and such that when less than all of the connectors of the two coupling devices are mutually engaged, fluid is permitted to flow out from either of the respective ports thereby causing a leak. A first of the coupling devices may have at least one interfering element that interferes with at least one interfering element of a second of the coupling devices such that both the first coupling device connectors cannot be sealingly engaged with both the second coupling device connectors. A first one or more of the coupling devices may be attached to containers of fluid to form access ports for removing fluid from the containers and the contents of the containers of fluid are different. A fluid circuit may have a coupling device that is compatible with the first one or more and incompatible with a second coupling device attached to a container of fluid.

According to embodiments, the disclosed subject matter includes a method of preventing the connection of a first coupling device to a second coupling device. The method includes providing a coupling device having a body with a single port with one opening at a first end, a double port with two openings at a second end, the single port and the double port is interconnected for fluid communication by a branching channel. The method includes attaching the single port to a source of fluid and providing the source of fluid to a site of usage. The sizes and connections between the openings are such that any attempt to connect one of the two openings of the double port to a fluid receiver and attempting to pass fluid from the source of fluid to the fluid receiver would result in a substantial leakage of fluid.

According to embodiments, the disclosed subject matter includes a fluid coupling system. The system includes a first coupling device with a first body and a second coupling device with a second body. The first body has a single port with one opening at a first end, a double port with two openings at a second end, the single port and the double port is interconnected for fluid communication by a branching channel in said body. The second body has a single port with one opening at a first end, a double port with two openings at a second end, the single port and the double port is interconnected for fluid communication by a branching channel in said body. The first body double port is configured to connect to the second body double port to form a sealed channel connecting the first body single port to the second body single port. The first and second coupling devices may be identical. The first and second coupling devices may be configured to allow frictional engagement of the first body two openings with the second body two openings to form the sealed channel. The first body may carry at least one first latch member and second body carries at least one second latch member, the first latch member is configured to interferingly engage the second latch member to increase the resistance of the first and second coupling devices to disconnection. The first latch member may be movable relative to the major portion of the first body to permit release of an engagement of the first and second latch members. The first body double port may have a male cylindrical fitting and a female cylindrical fitting, the first body two openings each is in a respective one of the two openings.

According to embodiments, the disclosed subject matter includes a fluid line coupling device kit having a first coupling device having at least two male and/or female connectors. The kit includes a second coupling device having at least two male and/or female connectors that are configured to sealingly engage with at least two male and/or female connectors of the first coupling device. Each of the first and second coupling devices is configured such that the every one of the at least two male and/or female connectors is fluidly coupled to a single respective port of said each of the first and second coupling devices. Each of the first and second coupling devices is configured further such that, when said second coupling device at least two male and/or female connectors are configured to sealingly engage with the at least two male and/or female connectors of the first coupling device, flow from the single respective port of the first coupling device flows through both of the at least two male and/or female connectors of each of the first and second coupling devices to the single respective port of the second coupling device. A latch component each of the first and second coupling devices may be configured mutually to engage when said second coupling device at least two male and/or female connectors are configured to sealingly engage. A third and a fourth coupling device may each have at least two male and/or female connectors that are configured to sealingly engage with at least two male and/or female connectors of the other of the third and fourth coupling devices and further configured such that at least both of the third and fourth coupling devices are incapable of sealingly engaging with the at least two male and/or female connectors of either of the first and second coupling devices. The third fourth coupling devices may be configured with interference members that permit them to be interconnected with each other but which prevent them from is interconnected with either of the first and second coupling devices and further configured such that the at least two male and/or female connectors of at least one of the third and fourth coupling devices are, but for an engagement by the interference member, capable of sealingly engaging the at least two male and/or female connectors of at least one of the first and second coupling devices. The first and second coupling devices may be identically configured to permit them to be molded from the same mold. The disclosed subject matter includes a method for molding in accord therewith. The first and second coupling devices may be configured such that they can be molded with a two part mold.

According to embodiments, the disclosed subject matter includes a method of conveying fluid. The method includes connecting a first source channel to a first destination channel to form a continuous flow path. The method includes flowing fluid through the first source channel into the first destination channel, the flowing including splitting the flow into separate branching flows and then recombining the flows at a junction between the source channel and destination channel. The method may include providing a kit with the first source channel and the first destination channel as well as a second source and a second destination channel and preventing connection of the first source channel to the second destination channel. The preventing may include leaking one of the branching flows in the event the first source channel is connected to the second destination channel or the second source channel is connected to the first destination channel. The preventing may include leaking an entirety of one of the branching flows in the event the first source channel is connected to the second destination channel or the second source channel is connected to the first destination channel. The preventing may include ensuring the a predefined orientation of coupling devices, used in the connecting, is required in order to prevent the leaking of an entirety of one of the branching flows and as a result of this orientation, an interfering portion of said coupling device attached to the first source channel is brought into interfering engagement with a portion of a coupling device attached to the second destination channel or an interfering portion of said a coupling device attached to the second source channel is brought into interfering engagement with a portion of a coupling device attached to the first destination channel.

According to embodiments, the disclosed subject matter includes a kit having fluid circuits that ensure against improper interconnection of fluid lines. The kit includes devices with fluid channels that convey fluid and coupling devices configured to interconnect the channels. The coupling devices are configured to be oriented in such a way as to sealingly engage multiple connectors of each coupling device pair such that which when connected each coupling device pair divides a flow through a respective coupling device and reunites the flow at an end of the respective coupling device pair, the arrangement of the connectors is such as to limit the possible orientations of the coupling devices with respect to coupling devices to which they interconnect. The coupling devices may be configured with interfering elements that mutually interfere when an attempt is made to align the multiple connectors of a coupling device pair for mutual sealing engagement. The coupling device pairs can be interconnected are configured to require the alignment of the axes of each member of a coupling device pair so that they are parallel. The coupling device pairs that can be interconnected may be configured to require the positioning of the multiple connectors of each coupling device on respective common axes thereof. The coupling devices may include interfering elements arranged such that when certain pairs of the coupling devices are oriented so that the connectors are mutually aligned so as to make it possible for them to sealingly engage, the orientation creates mutual interference of the coupling devices that prevents their interconnection. The coupling devices may include interfering elements arranged such that when certain pairs of the coupling devices are oriented so that the connectors are mutually aligned so as to make it possible for them to sealingly engage, the orientation positions the interfering elements so that they do not interfere thereby allowing the certain pairs to be interconnected.

According to embodiments, the disclosed subject matter includes a method of ensuring against improper interconnection of fluid circuits. The method includes providing a kit including devices with channels that convey fluid and coupling devices for interconnecting the channels. The method further includes orienting at least one of the coupling devices in such a way as to sealingly engage multiple connectors of each coupling device pair such that which when connected each coupling device pair divides a flow through a respective coupling device and reunites the flow at an end of the respective coupling device pair, the arrangement of the connectors is such as to limit the possible orientations of the coupling devices with respect to coupling devices to which they interconnect. The at least one of the coupling devices may be part of a multiple coupling device arrangement including ones which, when connected, do not divide a flow therethrough. The multiple coupling device arrangement coupling devices may be rigidly interconnected so as to position and orient all member coupling devices thereof with respect to respective paired coupling devices, simultaneously. The multiple coupling device arrangement may include a manifold that is configured to selectively couple for fluid communication among the coupling devices thereof. The multiple coupling device arrangement may include coupling devices that have separate fluid channels. The orienting may include positioning interfering elements of each coupling device pair such that the members of the coupling device pair can be brought together, without mutual interference of the interfering elements, when the multiple connectors of each coupling device pair are sealingly engaged. The orienting may include aligning the axes of each member of a coupling device pair so that they are parallel. The aligning may position the multiple connectors of each coupling device on respective common axes thereof. The method may include providing multiple coupling devices having interfering elements of the coupling devices arranged such that orienting respective pairs of the coupling devices to sealingly engage their connectors results in mutual interference of the coupling devices, which prevents their interconnection. The orienting may include positioning interfering elements of certain coupling device pair such that they interfere when the multiple connectors of each coupling device pair are positioned with their respective axes aligned so as to be capable of sealingly engaging each other, thereby preventing interconnection of said certain coupling device pairs.

According to embodiments, the disclosed subject matter includes a system for preventing misconnection of material conveyances. The system includes a set of coupling devices wherein each coupling device of the set has N fluid channels for outputting or receiving a material such as a fluid. Each coupling device the set having N+1 connectors connected to said N material channels such that at least one of the N material channels is furcated and connects with multiple connectors. Each coupling device of the set is configured to connect its N+1 connectors with at least N+1 connectors of at least one other coupling device of the set without leaking from one of the N+1 connectors. Each coupling device of the set is configured to prevent the connection of its N+1 connectors with the at least N+1 connectors of at least a further coupling device of the set without leaking from one of the N+1 connectors. The result is that the set forms a variety of coupling devices capable of forming a variety of unique coupling pairs of coupling devices and thereby prevent misconnection of coupling devices. The first coupling devices of the set may have interfering members that are positioned, shaped, and sized to interfere with second coupling devices of the set. The first coupling devices of the set may have interfering members that are positioned, shaped, and sized to interfere with second coupling devices of the set when the N+1 connectors are positioned to connect with N+1 connectors of another coupling device of the set, such that the first coupling devices are unable to be coupled to the second coupling devices.

The connectors can include any suitable type of connector, for example, they may include male and female connectors, butt-type connectors, and/or needle and septum type connectors. Illustrations of these are shown in the drawings and further examples may be found in the prior art. It is believed that simple substitution of many of the variety of connectors available in the art can be made readily to extend the range of possible embodiments of the disclosed subject matter. Some of the coupling devices of the set may have connectors that are configured to prevent a leak by blocking a connector of at least one of the N materials channels that is furcated and with which it is connected. Some of the coupling devices of the set may have connectors that are configured to prevent a leak by forming a continuous furcated channel for receiving material from, or conveying material to, connectors of furcated channels. The coupling devices may be configured such that when the N+1 connectors of one coupling device are connected with another and a flow of material between the one and another coupling devices is established, at least a portion of the flow is divided through one of the furcating channels thereof. The coupling devices may be configured such that when the N+1 connectors of one coupling device are connected with another and a flow of material between the one and another coupling devices is established, at least a portion of the flow is blocked that would otherwise flow out through one of the furcating channels thereof.

According to embodiments, the disclosed subject matter includes a method for providing a safety system. The method includes providing exclusively, for use in a predetermined set of processes or for use with a predetermined set of devices, coupling devices conforming to the systems of claims 45 to 52. A predefined subset of said set of fluid coupling devices may be exclusively connected to a predefined class of material containers. A predefined subset of said set of fluid coupling devices may be exclusively connected to a predefined class of medical devices.

According to embodiments, the disclosed subject matter includes system for interconnecting material-conveying elements. The system includes a set of coupling devices forming unique inter-connectable pairs, thereby forming sets of compatible and incompatible coupling devices. The system further includes containers and other sources of medical fluids with pre-attached ones of said set of coupling devices. The system includes medical devices with further pre-attached ones of said set of coupling devices. Each coupling device is configured to pass fluid through at least one internal flow channel therein, when connected to a compatible coupling device, and to leak fluid from said at least one internal flow channel, if connected to an incompatible coupling device.

According to embodiments, the disclosed subject matter includes a method of ensuring against improper interconnection of fluid lines. The method includes providing a kit including devices with channels that convey fluid and coupling devices for interconnecting the channels. The method also includes orienting at least some of the coupling devices in such a way as to sealingly engage multiple connectors of each coupling device pair such that which when connected each coupling device may have a furcated channel pair divides a flow through a respective coupling device and a connected coupling device with a further furcated channel reunites the flow at an end of the respective coupling device pair, the arrangement of the connectors is such as to limit the possible orientations of the coupling devices with respect to coupling devices to which they interconnect. At least one of the coupling devices includes at least one non-furcated channel of the pair of coupling devices connects by a single connector to a non-furcated channel on the other of the pair. The orienting may include positioning interfering elements of each coupling device pair such that the members of the coupling device pair can be brought together, without mutual interference of the interfering elements, when the multiple connectors of each coupling device pair are sealingly engaged. The orienting may include aligning the axes of each member of a coupling device pair so that they are parallel. The aligning may position the multiple connectors of each coupling device on respective common axes thereof. The providing may include providing multiple coupling devices having interfering elements of the coupling devices arranged such that orienting respective pairs of the coupling devices to sealingly engage their connectors results in mutual interference of the coupling devices, which prevents their interconnection. The orienting may include positioning interfering elements of certain coupling device pair such that they interfere when the multiple connectors of each coupling device pair are positioned with their respective axes aligned so as to be capable of sealingly engaging each other, thereby preventing interconnection of said certain coupling device pairs.

According to embodiments, the disclosed subject matter includes fluid channel coupling system. The system includes coupling devices, each having connectors that sealingly engage corresponding connectors on the other of the coupling devices. At least one of the coupling device connectors is in fluid communication with a common port such and the other having its connectors connected to a common port or a closure such that when the connectors of two coupling devices are mutually engaged, at least one of the respective ports is in fluid communication with another and such that when less than all of the connectors of the two coupling devices are mutually engaged, fluid is permitted to flow out from one of the respective ports thereby causing a leak. A first of the coupling devices may have at least one interfering element that interferes with at least one interfering element of a second of the coupling devices such that both the first coupling device connectors cannot be sealingly engaged with both the second coupling device connectors. A first one or more of the coupling devices may be attached to containers of fluid to form access ports for removing fluid from the containers and the contents of the containers of fluid are different. A fluid circuit may have a coupling device that is compatible with the first one or more and incompatible with a second coupling device attached to a container of fluid.

According to embodiments, the disclosed subject matter includes a method of preventing the connection of a first coupling device to a second coupling device. The method includes providing a first coupling device having a body with at least one port with one opening at a first end, and a double port with two openings at a second end, the single port and the double port is interconnected for fluid communication by a branching channel and attaching the single port to a source of fluid and providing the source of fluid to a site of usage. The sizes and connections between the openings are such that any attempt to connect one of the two openings of the double port to a fluid receiver and attempting to pass fluid from the source of fluid to the fluid receiver will result in a substantial leakage of fluid. The method further includes selecting a further coupling device of an apparatus to consume said fluid responsively to a compatibility of said further coupling device with the first coupling device, wherein the further coupling device may include two connectors that connect to said double port, at least one of the connectors is configured to providing a flow of fluid therethrough. The other of the connectors may be configured to block from out of at least one port of the double port.

According to embodiments, the disclosed subject matter includes a method of preventing the connection of a first coupling device to a second coupling device. The method includes providing a first coupling device having a body with at least one port with one opening at a first end, and a multiple port at a second end, the single port and the multiple port is interconnected for fluid communication by a branching channel to create a furcating flow therethrough and attaching the single port to a source of fluid and providing the source of fluid to a site of usage. The sizes and connections between the openings is such that any attempt to connect one of the two openings of the multiple port to a fluid receiver and attempting to pass fluid from the source of fluid to the fluid receiver will result in a substantial leakage of fluid. The method further includes selecting a further coupling device of an apparatus to consume said fluid responsively to a compatibility of said further coupling device with the first coupling device, wherein the further coupling device may include multiple connectors that connect to said multiple port, at least one of the connectors is configured to providing a flow of fluid therethrough. At least some of the connectors may be configured to block from out of at least one port of the multiple port.

According to embodiments, the disclosed subject matter includes a fluid coupling system. The system includes a first coupling device with a first body and a second coupling device with a second body. The first body has a single port with one opening at a first end and multiple ports with multiple openings at a second end, the single port and the multiple ports is interconnected for fluid communication by a branching channel in said body. The second body has a single port with one opening at a first end, multiple port with multiple openings at a second end, the single port and the multiple port is interconnected for fluid communication by a branching channel in said body. The first body double port may be configured to connect to the second body multiple port to form a sealed channel connecting the first body single port to the second body single port. The first body may include one or more further ports having non-branching channels that are automatically positioned and oriented for connection to further ports of the second body when the multiple ports of the first and second bodies are positioned and oriented for connection. The first and second coupling devices may be identical to permit the molding thereof with a single mold. The first and second coupling devices may be configured to allow frictional engagement of the first body two openings with the second body two openings to form the sealed channel. The first body may carry at least one first latch member and second body carries at least one second latch member, the first latch member is configured to interferingly engage the second latch member to increase the resistance of the first and second coupling devices to disconnection. The first latch member may be movable relative to the major portion of the first body to permit release of an engagement of the first and second latch members. The first body multiple port may have a male cylindrical fitting and a female cylindrical fitting, the first body two openings each is in a respective one of the two openings.

According to embodiments, the disclosed subject matter includes a fluid line coupling device kit. The kit includes a first coupling device having at least two male and/or female connectors and a second coupling device having at least two male and/or female connectors that are configured to sealingly engage with at least two male and/or female connectors of the first coupling device. At least one of the first and second coupling devices is configured such that the every one of the at least two male and/or female connectors thereof is fluidly coupled to a single respective port of said at least one of the first and second coupling devices. Ones of the first and second coupling devices is configured further such that, when said second coupling device at least two male and/or female connectors are configured to sealingly engage with the at least two male and/or female connectors of the first coupling device, and further configured such that a flow from the single respective port of the first coupling device flows through one or both of the at least two male and/or female connectors of the first coupling device to the single respective port of the second coupling device without leaking, at least one of the male and/or female connectors is configured to capture or block the flow from a connected one of the male and/or connectors. A latch component each of the first and second coupling devices may be configured mutually to engage when said second coupling device at least two male and/or female connectors are configured to sealingly engage. A third and a fourth coupling device each may have at least two male and/or female connectors that are configured to sealingly engage with at least two male and/or female connectors of the other of the third and fourth coupling devices and further configured such that at least both of the third and fourth coupling devices are incapable of sealingly engaging with the at least two male and/or female connectors of either of the first and second coupling devices. The third and fourth coupling devices may be configured with interference members that permit them to be interconnected with each other but which prevent them from is interconnected with either of the first and second coupling devices and further configured such that the at least two male and/or female connectors of at least one of the third and fourth coupling devices are, but for an engagement by the interference member, capable of sealingly engaging the at least two male and/or female connectors of at least one of the first and second coupling devices. The first and second coupling devices may be identically configured. The first and second coupling devices may be configured such that they can be molded with a two part mold.

According to embodiments, the disclosed subject matter includes a method of conveying fluid, connecting a first source channel to a first destination channel to form a continuous flow path. The method includes flowing fluid through the first source channel into the first destination channel, the flowing including splitting the flow into separate branching flows that flow through the connector at an interface thereof and then recombining the flows. The method may include providing a kit with the first source channel and the first destination channel as well as a second source and a second destination channel and preventing connection of the first source channel to the second destination channel. The preventing may include leaking one of the branching flows in the event the first source channel is connected to the second destination channel or the second source channel is connected to the first destination channel. The preventing may include leaking an entirety of one of the branching flows in the event the first source channel is connected to the second destination channel or the second source channel is connected to the first destination channel. The preventing may include ensuring the a predefined orientation of coupling devices, used in the connecting, is required in order to prevent the leaking of an entirety of one of the branching flows and as a result of this orientation, an interfering portion of said coupling device attached to the first source channel is brought into interfering engagement with a portion of a coupling device attached to the second destination channel or an interfering portion of said a coupling device attached to the second source channel is brought into interfering engagement with a portion of a coupling device attached to the first destination channel.

According to embodiments, the disclosed subject matter includes a kit having fluid circuits that ensure against improper interconnection of fluid lines. The kit includes devices with fluid channels that convey fluid and coupling devices configured to interconnect the channels. The coupling devices are configured to be oriented in such a way as to sealingly engage multiple connectors of each coupling device pair such that which when connected each coupling device pair divides a flow through a respective coupling device and either blocks or reunites the flow at an end of the respective coupling device pair, the arrangement of the connectors is such as to limit the possible orientations of the coupling devices with respect to coupling devices to which they interconnect. The coupling devices may be configured with interfering elements that mutually interfere when an attempt is made to align the multiple connectors of a coupling device pair for mutual sealing engagement. The coupling device pairs that can be interconnected may be configured to require the alignment of the axes of each member of a coupling device pair so that they are parallel.

According to embodiments, the disclosed subject matter includes a method of ensuring against improper interconnection of fluid circuits. The method includes providing a kit including devices with channels that convey fluid and coupling devices for interconnecting the channels and orienting at least one of the coupling devices in such a way as to sealingly engage multiple connectors of each coupling device pair such that which when connected each coupling device pair divides a flow through a respective coupling device and blocks one of the flows or reunites the divided flow at an end of the respective coupling device pair, the arrangement of the connectors is such as to limit the possible orientations of the coupling devices with respect to coupling devices to which they interconnect. The at least one of the coupling devices may be part of a multiple coupling device arrangement including ones which, when connected, do not divide a flow therethrough. The multiple coupling device arrangement coupling devices may be rigidly interconnected so as to position and orient all member coupling devices thereof with respect to respective paired coupling devices, simultaneously. The multiple coupling device arrangement may include a manifold that is configured to selectively couple for fluid communication among the coupling devices thereof.

In all of the foregoing embodiments, the interfering elements may be devices that rely on magnetic or electrical forces to block the coupling of incompatible coupling devices. Also, magnetic forces may be used to provide orientation enforcement. In embodiments, permanent magnets are integrated in coupling device embodiments. For form selective interfering elements, they may be positioned and numbered in varying arrangements (or shaped, sized, or otherwise configured) to form a variety of compatible and incompatible species. Magnets may also provide a means for making the connection so the incompatible species may push each other away while compatible ones pull together to mate.

It is, thus, apparent that there is provided, in accordance with the present disclosure, methods, devices and systems for connecting fluid lines. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A method of making a coupling device for establishing a fluid connection between two fluid lines, the method comprising:
   providing a kit having at least a first connector with a first set of one or more configurable interference elements and a second connector, wherein the first connector and the second connector are not configured to connect to each other until the first set of one or more configurable interference elements are configured; and
   configuring the first set of one or more configurable interference elements in a first configuration that permits the first connector to connect with the second connector, wherein
   the one or more configurable interference elements are configured to form multiple interfering element configurations, and
   each configuration of the multiple interfering element configurations permits an interference-free connection to at least one second connector and prevents, by mechanical interference, connection to at least a third connector.

2. The method according to claim 1, wherein
   the second connector has a second set of the one or more configurable interference elements, and the method further comprises
   configuring the second set of the one or more interference elements into a second configuration which is compatible with the first configuration of the first connector.

3. The method according to claim 2, further comprising:
   connecting the first connector to the second connector and thereby establishing the fluid connection between the two fluid lines.

4. The method according to claim 1, wherein
   the first connector includes a plurality of holes at predetermined locations on the first connector.

5. The method according to claim 4, wherein
   the configuring of the one or more configurable interference elements includes inserting posts into the holes on the first connector.

6. The method according to claim 2, wherein
   the first connector includes a first plurality of holes at predetermined locations on the first connector,
   the second connector includes a second plurality of holes at locations corresponding to the predetermined locations on the first connector, and
   the configuring the first set of the one or more configurable interference elements of the first connector and the second set of the one or more configurable interference elements of the second connector includes inserting posts into holes on the first connector and into holes on the second connector such that the inserted posts on the first connector do not interfere with the inserted posts on the second connector.

7. A method of making a coupling device for establishing a fluid connection between two fluid lines, the method comprising:
   extracting an arrangement of interfering elements from a lookup table that identifies one or more compatible arrangements of the interfering elements on a first connector for every possible arrangement of the interfering elements on a second connector;
   providing a kit having at least the first connector with one or more configurable interference elements and a second connector with one or more configurable interference elements; and
   configuring the one or more configurable interference elements on the first connector and the second connector according to the arrangement extracted from the lookup table, the arrangement permitting interference-free connection between the first connector and the second connector and preventing, by mechanical interference, connection between the first connector and at least a third connector.

8. A method of making a coupling device, comprising:
   providing a kit having a coupling device platform with at least one fluid line connector and at least one configurable interference element that may be modified to form at least two different coupling device arrangements; and
   prior to connecting the at least one fluid line connector, modifying the configurable interference element to form one of the at least two different coupling device arrangements, wherein
   a first of said two different coupling device arrangements is adapted for connection to a first configuration of external coupling devices,
   a second of said two different coupling device arrangements is adapted for connection to a second configuration of external coupling devices, and the second of said two different coupling device arrangements is adapted to prevent, by interference caused by engagement of said at least one configurable interference element, connection to the first configuration of external coupling devices.

9. The method of claim 8, wherein the first of said two different coupling device arrangements is adapted to prevent, by interference caused by engagement of said at least one configurable interference element, connection to the second configuration of external coupling devices.

\* \* \* \* \*